United States Patent
Steipe et al.

(12)

(10) Patent No.: US 6,262,238 B1
(45) Date of Patent: Jul. 17, 2001

(54) PROCESS FOR MODIFYING THE STABILITY OF ANTIBODIES

(75) Inventors: Boris Steipe, Gauting; Stefan Steinbacher, Lenggries, both of (DE)

(73) Assignee: Roche Diagnostic, GmbH, Mannheim (DE)

( * ) Notice: Subject to any disclaimer, the term of this patent is extended or adjusted under 35 U.S.C. 154(b) by 0 days.

(21) Appl. No.: 09/157,370

(22) Filed: Sep. 21, 1998

Related U.S. Application Data

(62) Division of application No. 08/765,179, filed on Jan. 14, 1997.

(51) Int. Cl.[7] .................. A61K 39/395; C12N 15/00; C12N 15/13
(52) U.S. Cl. ................. 530/387.3; 435/69.6; 424/133.1; 424/134.1; 530/387.3
(58) Field of Search ................ 435/69.6; 424/134.1, 424/133.1; 530/387.3

(56) References Cited

U.S. PATENT DOCUMENTS 6,054,297 * 4/2000 Carter et al. .................. 435/69.6

FOREIGN PATENT DOCUMENTS

WO 90/07861 * 7/1990 (WO) .................. C12P/12/00

OTHER PUBLICATIONS

Rudikoff et al, "Single amino acid substitution altering antigen–binding specificity.", PNAS, Vo. 79, pp. 1979–1983, Mar. 1982.*

Panka et al, "Variable region framework differences result in decreased or increased affinity of variant anti–digoxin antibodies." PNAS, vol. 85, pp. 3080–3084, May 1988.*

* cited by examiner

Primary Examiner—Geetha P. Bansal
Assistant Examiner—Karen A Canella
(74) Attorney, Agent, or Firm—Arent Fox Plotkin Kintner Kahn

(57) ABSTRACT

Process for the production of a functional immunoglobulin or functional derivative or fragment thereof with an improved stability in a eukaryotic or prokaryotic organism by transformation with an expression vector which contains a recombinant gene which codes for the said immunoglobulin derivative or fragment which is characterized in that a modified gene is used which contains at least one codon which is substituted compared to the unmodified gene and codes for a more frequent amino acid. In this way it is also possible to produce active antibodies free of disulfide bridges. In a modification of the process it is possible to selectively destabilize antibodies.

17 Claims, 2 Drawing Sheets

SEQUENCE LISTING

<160> NUMBER OF SEQ ID NOS: 10

<210> SEQ ID NO 1
<211> LENGTH: 117
<212> TYPE: PRT

<213> ORGANISM: Homo sapiens

<400> SEQUENCE: 1

```
Glu Val Gln Leu Val Glu Ser Gly Gly Leu Val Lys Pro Gly Gly
 1               5                  10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Gly Trp Ile Tyr Asn Gly Gly Asp Thr Tyr Tyr Ala Asp Ser Val Lys
    50                  55                  60

Gly Arg Phe Thr Ile Ser Arg Asp Thr Ser Lys Asn Thr Leu Tyr Leu
65                  70                  75                  80

Gln Met Asn Ser Leu Arg Ala Glu Asp Thr Ala Val Tyr Tyr Cys Ala
                85                  90                  95

Arg Gly Gly Gly Gly Tyr Phe Asp Tyr Trp Gly Gln Gly Thr Leu
            100                 105                 110

Val Thr Val Ser Ser
        115
```

<210> SEQ ID NO 2
<211> LENGTH: 117
<212> TYPE: PRT
<213> ORGANISM: Mus sp.

<400> SEQUENCE: 2

```
Glu Val Gln Leu Gln Gln Ser Gly Gly Glu Leu Val Lys Pro Gly Ala
 1               5                  10                  15

Ser Val Lys Leu Ser Cys Lys Ala Ser Gly Tyr Thr Phe Thr Ser Tyr
            20                  25                  30

Tyr Met His Trp Val Lys Gln Arg Pro Gly Lys Gly Leu Glu Trp Ile
        35                  40                  45

Gly Arg Ile Asn Pro Gly Ser Gly Gly Thr Asn Tyr Asn Glu Lys Phe
    50                  55                  60

Lys Gly Lys Ala Thr Leu Thr Arg Asp Lys Ser Ser Ser Thr Ala Tyr
65                  70                  75                  80

Leu Gln Leu Ser Ser Leu Thr Ser Glu Asp Ser Ala Val Tyr Tyr Cys
                85                  90                  95

Ala Arg Gly Gly Tyr Tyr Tyr Phe Asp Tyr Trp Gly Gln Gly Thr Thr
            100                 105                 110

Val Thr Val Ser Ser
        115
```

<210> SEQ ID NO 3
<211> LENGTH: 109
<212> TYPE: PRT
<213> ORGANISM: Homo sapiens

<400> SEQUENCE: 3

```
Asp Ile Gln Met Thr Gln Ser Pro Ser Ser Leu Ser Ala Ser Val Gly
 1               5                  10                  15

Asp Arg Val Thr Ile Thr Cys Arg Ala Ser Gln Ser Ile Ser Ser Tyr
            20                  25                  30

Leu Ala Trp Tyr Gln Gln Lys Pro Gly Lys Ala Pro Lys Leu Leu Ile
        35                  40                  45

Tyr Asp Ala Ser Asn Leu Glu Ser Gly Val Pro Ser Arg Phe Ser Gly
    50                  55                  60
```

```
Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Tyr Tyr Ser Leu Pro Tyr
                 85                  90                  95

Thr Phe Gly Gln Gly Thr Lys Val Glu Ile Lys Arg Thr
            100                 105
```

<210> SEQ ID NO 4
<211> LENGTH: 108
<212> TYPE: PRT
<213> ORGANISM: Mus sp.

<400> SEQUENCE: 4

```
Asp Ile Val Met Thr Gln Ser Pro Ala Ser Leu Ser Ala Ser Leu Gly
  1               5                  10                  15

Glu Arg Val Thr Ile Thr Cys Arg Ala Ser Gln Ser Val Ser Ser Tyr
                 20                  25                  30

Leu His Trp Tyr Gln Gln Lys Pro Gly Gln Ser Pro Lys Leu Leu Ile
             35                  40                  45

Tyr Arg Ala Ser Asn Leu Ala Ser Gly Val Pro Asp Arg Phe Ser Gly
 50                  55                  60

Ser Gly Ser Gly Thr Asp Phe Thr Leu Thr Ile Ser Ser Val Glu Ala
 65                  70                  75                  80

Glu Asp Leu Ala Thr Tyr Tyr Cys Gln Gln Ser Asn Ser Tyr Pro Tyr
                 85                  90                  95

Thr Phe Gly Gly Gly Thr Lys Leu Glu Ile Lys Arg
            100                 105
```

<210> SEQ ID NO 5
<211> LENGTH: 109
<212> TYPE: PRT
<213> ORGANISM: Homo sapiens

<400> SEQUENCE: 5

```
Gln Ser Glu Leu Thr Gln Pro Pro Ser Val Ser Val Ser Pro Gly Gln
  1               5                  10                  15

Thr Val Thr Ile Ser Cys Ser Gly Asp Ser Leu Gly Ile Gly Tyr Val
                 20                  25                  30

Ser Trp Tyr Gln Gln Lys Pro Gly Gln Ala Pro Lys Leu Val Ile Tyr
             35                  40                  45

Asp Asp Asn Lys Arg Pro Ser Gly Ile Pro Asp Arg Phe Ser Gly Ser
 50                  55                  60

Lys Ser Gly Asn Thr Ala Ser Leu Thr Ile Ser Gly Leu Gln Ala Glu
 65                  70                  75                  80

Asp Glu Ala Asp Tyr Tyr Cys Gln Ser Trp Asp Ser Ser Ser Val Val
                 85                  90                  95

Phe Gly Gly Gly Thr Lys Leu Thr Val Leu Gly Gln Pro
            100                 105
```

<210> SEQ ID NO 6
<211> LENGTH: 112
<212> TYPE: PRT
<213> ORGANISM: Mus sp.

<400> SEQUENCE: 6

```
Gln Ala Val Val Thr Gln Glu Ser Ala Leu Thr Thr Ser Pro Gly Glu
  1               5                  10                  15
```

```
Thr Val Thr Leu Thr Cys Arg Ser Ser Thr Gly Ala Val Thr Thr Ser
         20                  25                  30

Asn Tyr Ala Asn Trp Val Gln Glu Lys Pro Asp His Leu Phe Thr Gly
         35                  40                  45

Leu Ile Gly Gly Thr Asn Asn Arg Ala Pro Gly Val Pro Ala Arg Phe
     50                  55                  60

Ser Gly Ser Leu Ile Gly Asp Lys Ala Ala Leu Thr Ile Thr Gly Ala
 65                  70                  75                  80

Gln Thr Glu Asp Glu Ala Ile Tyr Phe Cys Ala Leu Trp Tyr Ser Asn
                 85                  90                  95

His Trp Val Phe Gly Gly Gly Thr Lys Leu Thr Val Leu Gly Gln Pro
             100                 105                 110

<210> SEQ ID NO 7
<211> LENGTH: 34
<212> TYPE: DNA
<213> ORGANISM: Artificial Sequence
<220> FEATURE:
<223> OTHER INFORMATION: Description of Artificial Sequence: synthetic
      oligodeoxynucleotide

<400> SEQUENCE: 7
ggtaacacgt tcacccagtg atacagacag agag                              34

<210> SEQ ID NO 8
<211> LENGTH: 33
<212> TYPE: DNA
<213> ORGANISM: Artificial Sequence
<220> FEATURE:
<223> OTHER INFORMATION: Description of Artificial Sequence: synthetic
      deoxynucleotide

<400> SEQUENCE: 8
ctgataccac gccaggtagt ttttctggtt acc                               33

<210> SEQ ID NO 9
<211> LENGTH: 34
<212> TYPE: DNA
<213> ORGANISM: Artificial Sequence
<220> FEATURE:
<223> OTHER INFORMATION: Description of Artificial Sequence: synthetic
      deoxynucleotide

<400> SEQUENCE: 9
accgctaccg ctacccgaga acggtccgg aaca                               34

<210> SEQ ID NO 10
<211> LENGTH: 33
<212> TYPE: DNA
<213> ORGANISM: Artificial Sequence
<220> FEATURE:
<223> OTHER INFORMATION: Description of Artificial Sequence: synthetic
      deoxynucleotide

<400> SEQUENCE: 10
cgggtaagag tggtcctgtt gacagtagta aac                               33
```

PROCESS FOR MODIFYING THE STABILITY OF ANTIBODIES

This application is a divisional of application Ser. No. 08/765,179, filed Jan. 14, 1997.

The invention concerns a process for modifying the stability of antibodies (AB) and their use especially in diagnostics and therapeutics.

Antibody biotechnology is a rapidly expanding field with focus on diagnostics (in vitro: e.g. antigen detection, in vivo: e.g. imaging) in therapy (in this case particularly humanized antibodies with increased serum half-life and reduced immunogenicity) and in toxicology (e.g. anti-digoxin antibodies as a specific antidote for a cardiac glycoside overdose). Further areas of application are under development for the induction of transplant tolerance (e.g. by anti-CD4 AB), for immunotherapy (e.g. CAMPATH in non-Hodgkin lymphoma) and for catalytic antibodies which in particular enable stereoselective and regioselective catalysis.

Natural antibody sequences are not optimized for stability, genetically engineered sequence hybrids (e.g. humanized antibodies or single-chain Fv fragments) are frequently considerably destabilized. The consequences can for example be:

impeded refolding denaturation: (I) degradation and (II) immunogenicity even at 37° C. in vivo impaired avidity aggregation and loss of activity on storage In order to stabilize antibodies in solutions it is for example known that proteins from the DNAJ protein family (EP-A 0 556 726) or from the HSP90 protein family (EP-A 0 551 916) can be added. By contrast no process is known up to now by which antibodies can be stabilized by specific mutations of the amino acid sequence. It is indeed theoretically possible to introduce numerous point mutations in antibodies and to screen these mutants for stability. However, in the case of other proteins it has turned out that only one in $10^3$–$10^4$ mutants has an improved stability. Such screening methods are thus very tedious and in addition are limited to proteins which have identifiable functions such as enzymatic activity (Rollence, 1988; Chen, 1989; Turner, 1992; Risse, 1992; Arase, 1993).

The genes of the variable domains of immunoglobulins have undergone diverse changes due to multiple gene duplications and mutations during their development. They are optimized for the ability of antibodies to bind selectively and with high affinity (Tonegawa, 1983; Berek, 1988; French, 1989). In this process the sequences which code for the domains are randomly mutated and those B cells are selected and propagated which exhibit improved antigen binding (Berek, 1993). Although the optimization of the antigen binding ability plays a dominant role, the quality of an antibody depends on the sum total of numerous factors such as antigen affinity, domain stability, interaction between the heavy and light chain, variable and constant domains, protease sensitivity and the ability to export and secrete the antibodies from the cell. Accordingly natural antibodies are not necessarily optimized for stability.

It is known from Frisch (1994) that a human $V_k$ protein is destabilized after a substitution of cysteine 23 which prevents the formation of the cysteine 23/cysteine 88 disulfide bridge. This destabilization can be partially reversed again by a substitution of tryptophan 32 for histidine. However, this is only a chance result which moreover is not consistent with the teaching of the invention.

The reason for this is that the $V_k$ protein REI described by Frisch is not a $V_k$ domain fragment of a naturally occurring antibody but rather a protein which is overexpressed as such in a myeloma cell line. REI is a protein whose composition differs substantially from $V_k$ domains that are fragments of naturally occurring antibodies. REI has for example unusual amino acids at positions 50 (E) and 93 (Q). Due to the spatial arrangement of the amino acids it is presumably possible for a salt bridge to form between E 50 and H 32 and a hydrogen bridge to form between Q 92 and H 32. Such a hydrogen bridge bond which does not occur in natural antibodies then stabilize this $V_k$ protein.

The object of the invention is to provide a process which enables the stability of antibodies to be modified in such a way that these antibodies are specifically stabilized, destabilized or can be restabilized after destabilizing measures such as for example the removal of disulfide bridges.

The object of the invention is a process for the production of a functional antibody, functional derivative or fragment thereof with an improved stability in a eukaryotic or prokaryotic organism by transformation with an expression vector which contains a recombinant gene which codes for the said immunoglobulin, derivative or fragment characterized in that a) the gene of at least one of the variable domains of the immunoglobulin is compared with the consensus tables 1–6 and the table is selected which has the highest homology to this domain, b) at least one codon of an amino acid is replaced in the gene of this variable domain and namely aa) in the case that this amino acid is not mentioned at its position in this selected table 1 by a codon for one of the stated amino acids and/or bb) in the case that this amino acid is mentioned at its position in table 1, by a codon for one of the stated amino acids with a higher frequency, c) the prokaryotic or eukaryotic organism is transformed with the gene modified in this manner and the antibody, the fragment or derivative with the desired activity is expressed.

If necessary the antibody can be isolated from the organism and optionally purified according to methods familiar to a person skilled in the art.

In a preferred embodiment of the invention the process is carried out in such a manner that a) at least one codon for an amino acid is replaced in the gene of the variable domain of the heavy chain of humans and namely aa) in the case that this amino acid is not mentioned at its position in table 1, by a codon for one of the stated amino acids and/or ab) in the case that this amino acid is mentioned at its position in table 1, by a codon for one of the stated amino acids with a higher frequency, b) in the gene of the variable domain of the heavy chain of the mouse ba) in the case that this amino acid is not mentioned at its position in table 2, by a codon for one of the stated amino acids and/or bb) in the case that this amino acid is mentioned at its position in table 2, by a codon for one of the stated amino acids with a higher frequency, c) in the gene of the variable domain of the light chain of the kappa type of humans ca) in the case that this amino acid is not mentioned at its position in table 3, by a codon for one of the stated amino acids and/or cb) in the case that this amino acid is mentioned at its position in table 3, by a codon for one of the stated amino acids with a higher frequency, d) in the gene of the variable domain of the light chain of the kappa type of the mouse
   da) in the case that this amino acid is not mentioned at its position in table 4, by a codon for one of the stated amino acids and/or
   db) in the case that this amino acid is mentioned at its position in table 4, by a codon for one of the stated amino acids with a higher frequency, e) in the gene of the variable domain of the light chain of the λ type of humans
   ea) in the case that this amino acid is not mentioned at its position in table 5, by a codon for one of the stated amino acids and/or
   eb) in the case that this amino acid is mentioned at its position in table 5, by a codon for one of the stated amino acids with a higher frequency, f) in the gene of the variable domain of the light chain of the λ type of the mouse
   fa) in the case that this amino acid is not mentioned at its position in table 6, by a codon for one of the stated amino acids and/or
   fb) in the case that this amino acid is mentioned at its position in table 6, by a codon for one of the stated amino acids with a higher frequency, g) and the prokaryotic or eukaryotic organism is transformed and the antibody, the fragment or derivative with the desired activity is expressed.

The process according to the invention is used in such a manner that the antibody which it is intended to stabilize is firstly sequenced and the sequence of its domains is compared with the consensus sequences stated in tables 1–6 or the sequences of Kabat (1991). The amino acid positions are defined at a maximum homology of the sequences. Subsequently one or several codons can be modified according to the invention, advantageously by mutagenesis. It turns out that the specific substitution of one codon can already lead to a considerable change in the stability of an antibody. However, two, three or more codons are preferably modified. An upper limit for the number of substitutions is reached when other properties of the antibody which are important for the desired application purpose (e.g. affinity, protease stability, selectivity) are adversely affected.

It is intended to elucidate the procedure on the basis of an example: The amino acid positions are firstly determined by a sequence comparison (maximum homology) with tables 1–6 or with the tables of Kabat (1991).

In the case of a human antibody whose stability is not optimal it is found that the amino acid H is present at position 15 of the heavy chain. Table 1 shows that G or S is preferred at position 15. Accordingly it is advantageous to replace H by S or particularly preferably by G. If it is found that the amino acid A is located at position 16 in this antibody, then it is preferable to replace A by Q, R or G. Apparently it is particularly preferable to replace A by G.

If for example the antibody has an insertion of one or two amino acids after position 35, then it is preferable to delete at least one of these amino acids (replace 35a/35b by "–"). The same applies to the other optional insertions. Thus the tables should be interpreted such that the amino acids at positions which are denoted a, b etc. (e.g. 35a, 35b) are preferably deleted in order to stabilize the antibody (i.e. substituted by the amino acid "–"). In the case of position 100b in table 1 this means that for example an amino acid which is not mentioned can be substituted by G or S for stabilization. However, it is preferable to delete this amino acid. It is, however, equally advantageous to delete G or S at this position.

In order to stabilize an antibody by the process according to the invention and to nevertheless preserve its other properties such as especially affinity for the antigen, amino acids are preferably substituted which as far as possible do not impair these properties. For this reason it is preferable not to carry out any substitutions in the antigen binding loops or CDRs.

The antibody derivatives and fragments can be produced according to methods for the production of recombinant proteins familiar to a person skilled in the art. Such methods are described for example in EP-B 0 125 023 and EP-B 0 120 694 and in S. L. Morrison et al. (1984).

In order to produce the antibodies modified according to the invention it is for example possible to synthesize the complete DNA of the variable domain (by means of oligonucleotide synthesis as described for example in Sinha et al., NAR 12 (1984), 4539–4557). The oligonucleotides can be coupled by PCR as described for example by Innis, Ed. PCR protocols, Academic Press (1990) and Better et al., J. Biol. Chem. 267 (1992), 16712–16118. The cloning and expression is carried out by standard methods as described for example in Ausubel et al, Eds. Current protocols in Molecular Biology, John Wiley and Sons, New York (1989) and in Robinson et al., Hum. Antibod. Hybridomas 2 (1991) 84–93. The specific antigen binding activity can for example be examined by a competition test as described in Harlow et al., Eds. Antibodies; A Laboratory Manual, Chapter 14, Cold Spring Harbor Laboratory, Cold Spring Harbor (1988) and Munson et al., Anal. Biochem. 407 (1980), 220–239.

Suitable host organisms are for example CHO cells, lymphocyte cell lines which produce no immunoglobulins, yeast, insect cells and prokaryotes such as E. coli.

A further subject matter of the invention is such a process in which the protein is isolated in a prokaryotic organism (e.g E. coli) as denatured inclusion bodies and is activated by processes familiar to a person skilled in the art (cf. e.g. EP-A 0 364 926). In this process the activation can surprisingly also be carried out under reducing conditions.

A further subject matter of the invention is a process in which the antibody is stabilized according to the invention in such a way that it is biologically actively formed in the cytosol with the desired activity and can be isolated directly from this and in an active form.

The process according to the invention improves the stability of antibodies and antibody fragments for all the aforementioned areas of application. Moreover new stable antibody variants can be produced according to the invention which were previously not obtainable in a stable form such as antibodies free of disulfide bridges or catalytic antibodies which are suitable for use under unphysiological conditions. Catalytic antibodies and the use thereof are described for example in CIBA Foundation Symposium on Catalytic antibodies, London, 1990, Ed. Chadwick D. J., Marsh J., Volume 159, Wiley and Sons, Chichester.

Stabilized antibodies free of disulfide bridges are obtained by substituting the cysteines which form disulfide bridges by other amino acids and replacing at least one, and preferably two or more amino acids by stability-mediating amino acids.

Such antibodies are preferably chimeric, humanized, non-human or human antibodies that can be assigned to a β lymphocyte expression (no REI protein).

A further subject matter of the invention is a process for producing non-disruptive destabilized antibodies which can for example be advantageously used if rapid pharmacokinetics is required. In order to obtain such antibodies one must consequently carry out at least one amino acid substitution in the opposite manner to that described above. This means that an amino acid with a higher frequency is replaced by an amino acid with a lower frequency.

Suitable antibody fragments are for example Fab, Fab', F(ab')$_2$, single-chain antibodies, Fv or individual variable domains. These fragments can also be coupled to further substances for example to immunotoxins.

The process according to the invention is particularly advantageous for improving the stability of single-chain $F_v$ regions of antibodies in particular for improving the stability of single-chain immunotoxins. In such single-chain antigen-binding proteins the light and heavy chain are linked together in different ways. This linkage is for example achieved via a disulfide bridge, via covalent bonds or via a zinc complex bond. Such single-chain proteins and their linkage are described for example in Brinkmann et al., P.N.A.S. 89 (1992), 3075–3079 (linkage via a peptide linker), in Brinkmann et al., P.N.A.S. 90 (1993), 7536–7542 (additional disulfide bridge). Further immunotoxins and possibilities of linkage are described in WO 91/09871, WO 91/12820 and WO 91/16069.

A further advantage of the invention is that scF$_v$ (single chain F$_v$, hybrid proteins from V$_H$ and V$_L$ domains which are linked by an unstructured oligopeptide) can be produced according to the invention in a stable and less immunogenic form. The linker peptides (S. H. Jung (1994), R. Glockshuber (1990) of the scF$_v$s that are usually used frequently lead to aggregation problems and are potential immunogens. The covalent linkage of V$_H$ and V$_L$ domains can in contrast also be achieved by an intermolecular cystine bridge, but such additional cysteines have previously led to a considerable impairment of the folding yield due to the potential for forming false disulfide bridges. The process according to the invention enables the conserved cysteines at positions 23/88 (light chain), 22/99 (heavy chain) to be replaced by mutagenesis and the stability of the antibodies to be restored or improved by the process according to the invention. In this manner the formation of false disulfide bridges is excluded. The process according to the invention is therefore of major importance for the therapeutic use of recombinant antibody hybrids.

In addition antibodies can be tailor-made to suit a large number of effector functions by selection in the immune system. This natural protein engineering system has an unrivalled efficiency. The cytoplasmic expression of special functional antibody domains enables such effector functions to be introduced into the cells. Applications are advantageous which result in the modulation of the activity of cellular proteins. This can for example be achieved by stabilizing the target protein by protein-antibody complex formation. This can lead to a change in the degradation kinetics. Allosteric effector actions are also possible. The approximation of two effectors by the formation and stabilization of a ternary complex creates a further possibility for influencing metabolic paths for example by artificial multi-enzyme complexes or the local increase of metabolite concentrations of inducible operators. However, the cytoplasmic expression of catalytic antibodies is particularly advantageous and the associated possibility of selecting for catalytic efficiency. A cytoplasmic expression of functional antibodies can be accomplished in a simple manner for antibodies stabilized according to the invention.

A further advantage of the process according to the invention is that antibodies that are produced in an inactive form after expression can be activated under reducing conditions (e.g. DTE, DTT, glutathione).

The stabilized antibodies according to the invention can be used advantageously in all areas of application for antibodies for example in the therapeutics of cancer and infections, as an immunotoxin, for drug-targeting and in gene therapy. A use in imaging and in diagnostics is equally advantageous for example in order to analyse antigen-binding substances.

The process according to the invention is particularly advantageous for stabilizing antibodies which have already been modified for other reasons such as for example humanized or chimeric antibodies. This modification of the amino acids can result in a destabilization and the process according to the invention can restore or even improve the original stability of the antibodies by an additional modification of these antibodies outside the CDR regions.

Method for Analysing the Sequence Data Base and for Finding the Tables 1–6

(Canonical Sequence Approximation)

The invention assumes that the naturally occurring immunoglobulin sequences are a canonical collection of sequences whose sum total should be compatible for all aspects of antibody functions.

The amino acid which is observed most frequently in nature at a position should also be that which best stabilizes a protein; this applies particularly to proteins which are naturally selected for stability and not for special functions.

At the positions 35,37,39,44,45,47,50,91,95,100j, 100k, 101 and 103 of the heavy chain and 1,32,34,36,38,43,44,46,49,50,87,95,96 and 98 of the light chain of humans the amino acids are involved in important interactions in the formation of heterodimeric Fv fragments; here the selection is not primarily for stability. If the goal is to improve the dimerization properties, then the most frequent amino acids at these positions should be selected, if the goal is to improve the stability then it is also possible to select the second or third most frequent amino acids.

The natural frequencies of the amino acids are determined from a random sample from the immunoglobulin data base (Kabat, 1991). It is important that this random sample is a good representation of the actual ratios. For this reason it is also obvious that tables 1–6 can under certain circumstances be slightly modified when further additional data become available. According to the theory predictions can be made for the distribution within a species (e.g. human or mouse) and within a subtype (e.g. kappa or lambda).

Some closely related sequences are overrepresented in the data base for methodical reasons. A consequence is that the data base does not represent a suitable random sample without further modification. For this reason only the substantially complete sequences are selected from the data base in order to avoid problems with the definition of a sequence distance between sequences for which only fragments are known. Sequences are selected of which more than 75% of the positions are known corresponding to not more than 30 missing positions for the light chains and not more than 33 missing positions for the heavy chains. Thus the following sequences of the Kabat data base are used in the further analysis;

| Protein | Number |
| --- | --- |
| $V_L$-kappa, mouse | 731 of 1068 sequences |
| $V_L$-kappa, human | 127 of 319 sequences |
| $V_L$-lambda, human | 82 of 148 sequences |
| $V_L$-lambda, mouse | 63 of 74 sequences |
| $V_H$, human | 178 of 325 sequences |
| $V_H$, mouse | 883 of 1620 sequences |

In these sequences all paired sequence spacings are calculated and analysed. This typically results in a bimodal distribution with a maximum around the average spacing of all sequences of this subtype. This distribution of the spacing of the sequences can be used to reduce the effect of random sample errors: if the sequences of the natural distribution have a particular average spacing and a particular distribution of the spacing, random sample errors are reduced if a random sample is taken from the data base under the same boundary conditions of spacing distribution. The boundary conditions used are:

| Protein | least spacing | maximum spacing |
| --- | --- | --- |
| $V_L$-kappa, mouse | 25 | 57 |
| $V_L$-kappa, human | 25 | 57 |
| $V_L$-lambda, human | 33 | 65 |
| $V_L$-lambda, mouse | 8 | 26 |
| $V_H$, human | 37 | 77 |
| $V_H$, mouse | 37 | 77 |

For this sequences are selected at random from the data base and it is examined whether they fulfil a minimum and a maximum distance to the previously selected sequences. If this is the case they are classed with the new random sample. This is repeated until all sequences have been examined with regard to their suitability as a member of the random sample. Typically between 5 and 20% of the sequences of the data base are selected in this process. If this selection is often (in this case 500 times) repeated, each individual sequence will be represented in the random sample but with a different frequency depending on its distance to the other sequences. Finally this new random sample is used to determine the amino acid frequencies for the individual positions.

In the case of the frequencies determined here the resampling process described above was used whereby amino acids whose frequency is below 0.1 (=10%) are not listed in the tables.

The invention is described in more detail by the following examples, figures, tables and the sequence protocol.

(The plasmid corresponds essentially to the plasmid described in EP-B 0 324 162. This patent also describes the expression of antibodies using this plasmid).

Figure 1:
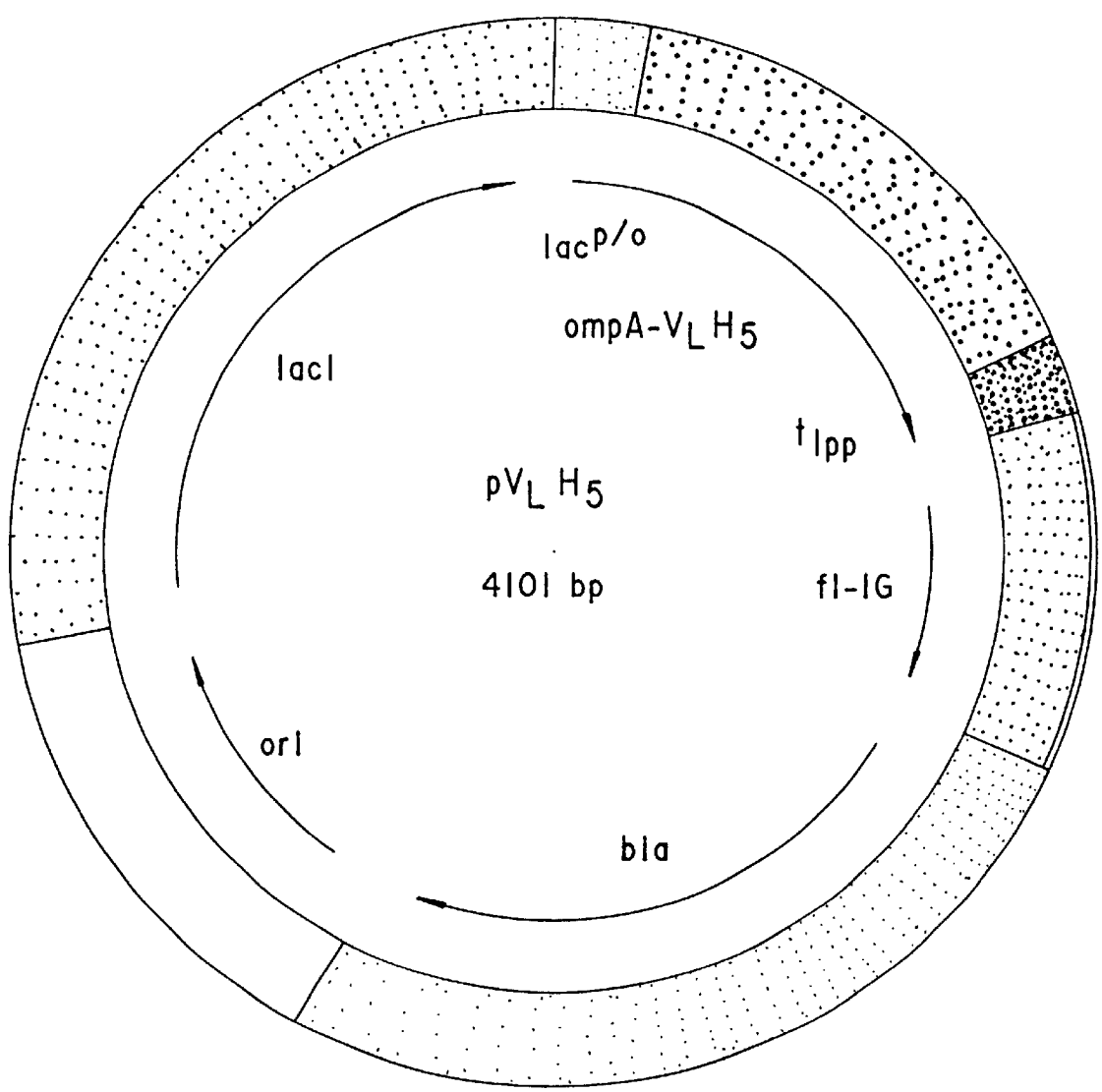
FIG. 1: Expression plasmid $pV_LH_5$ ($lac^{p/o}$: promoter/operator region of the lac gene; ompA $V_LH_5$ coding region for the $V_L$ domain with the signal sequence of the outer membrane protein A; $t_{lpp}$ terminator; f1-IG: F1 phage origin of replication; bla: gene of b lactamase; ori: plasmid origin of replication; lacI: gene of the lac repressor). The figure is not true to scale.
Figure 2:
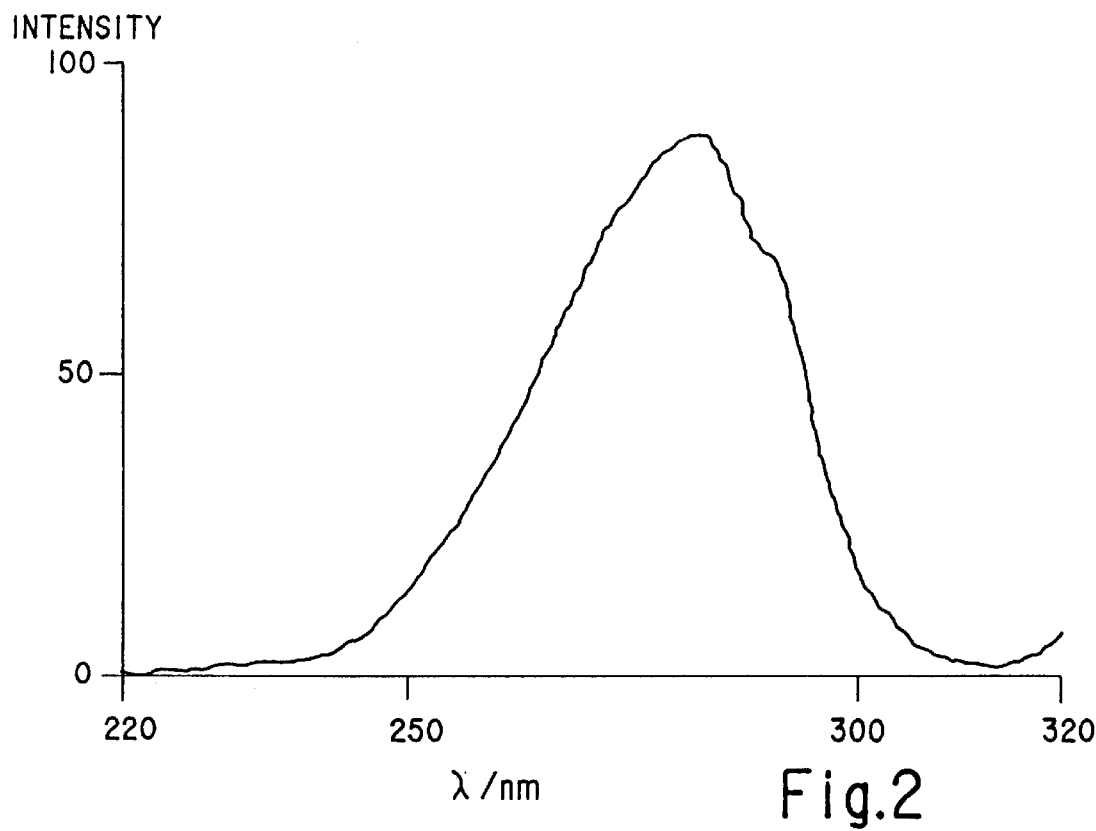

FIG. 2: Excitation spectrum of the $V_L$ protein. The emission is measured as $I_{Em}$=360 nm, protein concentration: 2 mM in PBS. The intensity is stated in arbitrary units.

Figure 3:
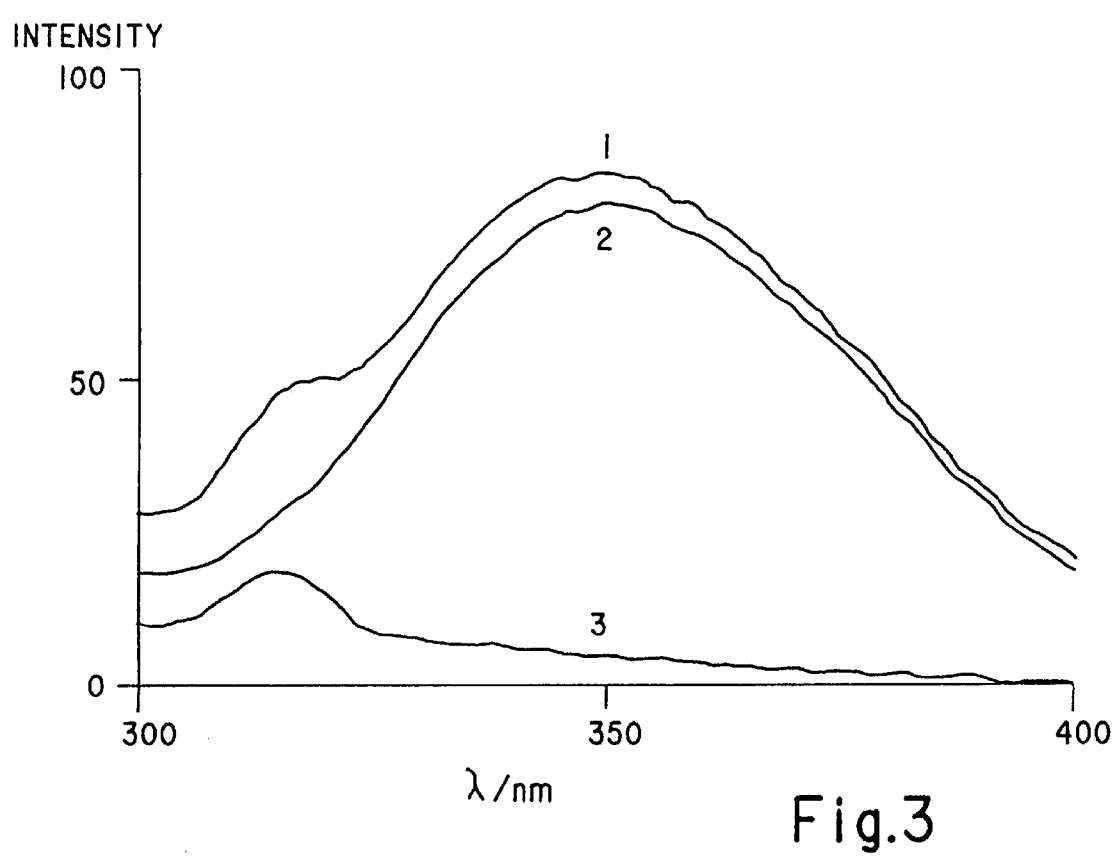

FIG. 3: Fluorescence spectrum of the folded (1), the unfolded (3) $V_L$ protein and the difference spectrum (2). Excitation wavelength $I_{Ex}$=284 nm. Protein concentration: 2 mM in PBS. The intensity is stated in arbitrary units.

EXAMPLES

| Bacteria and Phages | |
| --- | --- |
| *E. coli* K12 strains | |
| CJ236 | dut1, ung1, thi-1, relA1 [pCJ105 (Cam$^r$), F'] (Geisselsoder et al., 1987) from Bio-Rad Laboratories GmbH, Munich |
| JM83 | ara, D(lac-pro AB), strA, thi-1[F80lacZM15] (Yanisch-Perron et al. 1985] |
| JM109 | recAl, supE44, endAl, hsd R17, gyrA96, relAl, thi__(lac-pro AB) (Yanisch-Perron et al, 1985) |
| Bacteriophage | |
| M13K07 | Helper phage (Vieira & Messing, 1987) from Deutsche Pharmacia GmbH, Freiburg |

Plasmids

The plasmid $pV_LH_5$ codes for the $V_L$ domain of the antibody McPC603 under the control of the lac promoter/operator. In order to purify the protein to homogenicity in one step by chromatography on immobilized zinc ions, the two C-terminal amino acids arginine (108) and alanine (109) are replaced by five histidine residues. In contrast to the wild-type sequence a leucine residue is located at position 106 instead of an isoleucine residue.

For the secretion into the periplasma the signal sequence of the outer membrane protein A is inserted in front of the coding region of $V_L$ (Skerra & Plückthun 1989).

Oligodeoxynucleotides

The oligodeoxynucleotides used were synthesized by the phosphoramidite process on a DNA synthesizer 380A from Applied Biosystems GmbH, Weiterstadt.

(SEQ ID NO:7)
LD 38 (A15L) 5'-GGT AAC ACG TTC ACC CAG TGA TAC AGA CAG AGA G (SEQ ID NO:8)
LD 40 (F32T) 5'-CTG ATA CCA CGC CAG GTA GTT TTT CTG GTT ACC (SEQ ID NO:9)
LD 42 (T63S) 5'-ACC GCT ACC GCT ACC CGA GAA ACG GTC CGG AAC A (SEQ ID NO:10)
LD 44 (N90Q) 5'-CGG GTA AGA GTG GTC CTG TTG ACA GTA GTA AAC

Propagation of *E. coli* Cultures (Maniatis et al. 1982)

A dense overnight culture is obtained after incubation at 37° C. with shaking at 180 to 200 rpm for 14 to 20 hours. The cell density is determined by measurement of the $OD_{600}$. In order to select for strains carrying plasmid a suitable antibiotic is added to the medium.

LB medium:
  10 g/l Bacto-tryptone
  5 g/l Bacto-yeast extract
  5 g/l NaCl
  2.5 ml/l 1 M NaOH Transformation of E. coli with Plasmid-DNA
(Hanahan, 1983)

Competent Cells

E. coli Cells are Made Competent for the Transformation

In a 250 ml Erlenmeyer flask 20 ml TYM medium is inoculated with 0.5 ml of a stationary overnight culture of the E. coli strain used and incubated at 37° C. up to an $OD_{600}$ of 0.2 to 0.8. This culture is added to 100 ml TYM medium. After growth to an $OD_{600}$ of 0.5 to 0.9 it is filled up to a total volume of 500 ml with TYM medium and further incubated. When an $OD_{600}$ of 0.6 is reached, the bacterial suspension is cooled.

The bacteria are centrifuged at 4200 rpm for 15 minutes at 4° C., the supernatants are decanted and the pellets are resuspended in a total of 80 ml TfB I buffer, centrifuged, the supernatants are decanted and the pellets are resuspended in a total of 16 ml ice-cold TfB II buffer.

| | |
|---|---|
| TYM: | 20 g/l Bacto-tryptone |
| | 5 g/l Bacto yeast extract |
| | 100 mM NaCl |
| | 10 mM $MgSO_4$ |
| TfB I: | 30 mM KOAc |
| | 50 mM $MnCl_2$ |
| | 100 mM KCl |
| | 10 mM $CaCl_2$ |
| | 15% (v/v) glycerol |
| TfB II: | 75 mM $CaCl_2$ |
| | 10 mM KCl |
| | 10 mM NaMOPS pH 7.0 |
| | 15% (v/v) glycerol |

Transformation

The plasmid DNA is added to a volume of 30 µl water and mixed well with the bacterial suspension. After 60 minutes on ice it is heat-shocked for 115 seconds at 37° C. After 1 minute on ice 800 µl LB medium is added, the bacterial suspension is transferred to a 10 ml culture tube and incubated for 60 minutes at about 180 rpm and 37° C. The total transformation mixture is poured onto a LB plate containing antibiotic and incubated for 12 to 16 hours at 37° C.

Mutagenesis

The mutagenesis is carried out using the buffer of the Muta-Gene™ in vitro mutagenesis kit (Bio Rad Laboratories GmbH, GER) according to Kunkel 1985, Geisseloder et al., 1987, Vieira and Messing, 1987.

Production of Double Mutations by Recloning DNA Fragments

In the course of determining the conformation stability of the individual mutants (2.3) Ala15Leu, Asn90Gln and Phe32Tyr proved among others to have a stabilizing effect. In order to investigate the additivity of the stabilizing effects the double mutants Ala15Leu/Asn90Gln and Ala15Leu/Phe32Tyr were produced.

The double mutants were prepared by recloning DNA fragments of individual mutants that had already been produced. After a restriction digestion the fragments were separated by agarose gel electrophoresis, the desired fragments were cut out of the agarose, the DNA was isolated therefrom and ligated in a suitable manner.

Ala15Leu/Phe32Tyr

Digestion of the plasmid DNA of the mutants Ala15Leu and Phe32Tyr with the restriction endonuclease Bst EII yielded two fragments in each case. A 3232 bp fragment contained the bases of amino acid 32 and a fragment of 870 bp contained the bases of amino acid 15. The difference of the free enthalpy of unfolding compared to the unmodified antibody was found to be 22.6 kJ/mol (20.8 in theory).

Ala15Leu/Asn90Gln

Digestion of the plasmid DNA of the mutants Als15Leu and Asn90Gln with the restriction endonuclease Xmn I yields two fragments in each case. A 2991 bp fragment contains the bases of amino acid 15 and a fragment of 1110 bp contains the bases of amino acid 90. The difference of the free enthalpy of unfolding compared to the unmodified antibody was found to be 23.9 kJ/mol (23.6 in theory).

Expression of Recombinant $V_L$ Domains and Processing

The $V_L$ proteins are expressed (Skerra and Plückthun 1988) under the control of the lac operator/repressor in Escherichia coli and the expression is induced with IPTG. The coding region of the protein is preceded by the signal sequence of the outer membrane protein A (ompA) which causes the protein to be secreted into the periplasma during which it is cleaved by an endogenous E. coli signal peptidase. The secretion into the periplasma enables the formation of the central disulfide bridge as a result of the higher (oxidizing) redox potential which is present there and thus the correct folding of the $V_L$ protein which is not possible in the cytoplasm due to the lower (reducing) redox potential (Gilbert 1990).

The protein can be easily isolated in the mixture with other periplasmatic proteins by a selective lysis of the periplasma (1 M NaCl/1 mM EDTA/50 mM Tris/HCL pH 8.0). The five C-terminal histidine residues which are present instead of the amino acids 108 and 109 enable a simple purification of the protein to homogeneity in one step by chromatography on immobilized zinc ions (Hochuli et al. 1988).

10 Liters LB medium is inoculated with 200 ml of a stationary overnight culture of E. coli JM 83/p $V_L H_5$ and admixed with 10 ml AMP stock solution. The culture is aerated and incubated at room temperature up to an $OD_{600}$ of 0.7 (about four hours).

In order to induce the $V_L H_5$ expression under the control of the lac operator/repressor 5 ml 1 M IPTG solution is added as well as 5 ml AMP stock solution which compensates the loss of selection antibiotic which is caused by the fact that lysed bacteria release β lactamase from the periplasma into the medium.

It is incubated for a further 3 hours. In order to harvest the bacteria about 430 ml portions are filled into 500 ml centrifuge cups for the rotor JA-10 of a Beckmann centrifuge and centrifuged at 6000 rpm for 10 minutes in each case. 4 centrifugations are necessary using 6 centrifuge cups.

After decanting the supernatants about 30 gram bacterial pellets are typically obtained.

Periplasma Lysis 2 ml periplasma lysis buffer is added per gram cells, the bacteria are resuspended at 4° C. while stirring and stirred vigorously for at least one further hour. Subsequently the milky light-brown suspension is transferred into centrifuge cups for the rotor JA-20 of a Beckmann centrifuge and the spheroblasts are separated by 20 minutes centrifugation at 20,000 rpm at 4° C. The clear, light-yellow supernatant containing the recombinant $V_L$ protein is transferred into 50 ml Falcon vessels and stored until use at 4° C.

Chromatography on Immobilized Zinc Ions (Hochuli et al. 1988, Lindner et al. 1992)

The five C-terminal histidine residues of the $V_L$ domain increase the binding of the protein to immobilized zinc ions to such an extent that it can be purified to homogeneity in one step. In this case the zinc is complexed to an iminodiacetate chelate ligand which is in turn coupled to Sepharose. The histidine residues of the protein now act as complex ligands on the zinc and are thus bound to the column material. The elution can be achieved with imidazole which displaces the histidine residues on the zinc.

Preparation of the Column

In order to regenerate the column (about 5 ml chelating Sepharose Fast Flow from the German Pharmacia GmbH, Freiburg) it is firstly rinsed with 50 ml regeneration buffer and then with 20 ml water in order to remove complexed zinc and thus proteins which may still be bound. Subsequently the column is rinsed with 15 ml zinc chloride solution (1 mg/ml), 15 ml water and 50 ml column equilibration buffer.

Chromatography

The chromatography is carried out at a flow rate of about 0.7 to 1 ml/min and fractions of 10 minutes in each case are collected.

After applying the periplasma lysate (typically about 70 ml) it is rinsed with column equilibration buffer until the $OD_{280}$ has returned to the zero value. Weakly bound proteins are eluted by rinsing with 10 mM imidazole in column equilibration buffer. The $V_L H_5$ domain is eluted in a linear gradient of 10 to 300 mM imidazole in column equilibration buffer and a total volume of 200 ml at about 70 mM imidazole. The purity of the protein is checked by SDS polyacrylamide gel electrophoresis.

| Periplasma lysis buffer: | 1M NaCl |
| | 1 mM EDTA |
| | 50 mM Tris/HCl pH 8.0 |
| Column equilibration buffer: | 1M NaCl |
| | 50 mM Tris/HCl pH 8.0 |
| Regeneration buffer: | 1M NaCl |
| | 50 mM EDTA |
| | 50 mM Tris/HCl pH 8.0 |

Subsequently the protein solution which contains the desired amount of $V_L$ protein (about 1 to 2 mg) is dialysed twice against the 100-fold volume of the corresponding buffer.

Determination of Denaturation Curves

In order to determine denaturation curves the $V_L$ protein is dialysed against PBS and adjusted to a concentration of 0.2 mM (2.5 mg/ml; M=12.4 kDa). In order to remove precipitates and other particles from the protein solution this is centrifuged before use for 10 minutes in a refrigerated Sigma 2K15 centrifuge and the supernatant is transferred into a new 1.5 ml Eppendorf reaction vessel. 5 µl aliquots of this protein solution are placed in a 5 ml test tube using a 10 µl Hamilton pipette and admixed with 500 µl denaturation buffer, the test tube is closed with a silicone stopper and incubated overnight at 20° C.

Guanidinium chloride solutions in PBS in a concentration range of 0 to 5 M serve as the denaturation buffer. After 2 M the concentration is increased in steps of 0.1 M and beyond that in steps of 0.2 M.

| Instrument settings: | |
| --- | --- |
| Excitation wavelength: | $l_{Ex}$ = 284 nm |
| Emission wavelength: | $l_{Em}$ = 360 nm |

-continued

| Instrument settings: | |
| --- | --- |
| Excitation slit width: | 2 nm |
| Emission slit width: | 10 nm |

2.3 Analysis of Denaturation Curves to Determine the Free Enthalpy of Unfolding

In the presence of denaturing compounds proteins lose their native conformation and thus their biological function. Urea and guanidinium chloride are particularly effective for this. Many soluble globular proteins can be reversibly unfolded by these compounds and exhibit a simple two-state behaviour. This can be shown by comparing calorimetric data ($DH_{cal.}$) with the corresponding van t'Hoff enthalpies ($DH_{van\ t'Hoff}$), which can be determined from the temperature-dependency of the equilibrium constants. The ratio of the two should be one. It was shown that deviations from this are very small in the case of a large number of single domain proteins. This shows that intermediates that may occur are thermodynamically unstable. One can therefore ignore them and consequently regard the denaturation as a cooperative transition between two macroscopic states the folded (F) and the unfolded (U) (Privalov 1979).

In this case the unfolded protein represents an ensemble of conformers which can be rapidly converted into one another which have an identical or very similar energy. In the ideal case the denatured state would form a random coil i.e. the rotation around bonds should be completely free and independent of the rotation of all neighbours. Since interactions between the solvent, the main chain atoms of the protein and the 20 different side chains of the amino acids cannot be ideal in the same manner, a behaviour which deviates from the ideal random coil would be expected (Tanford 1970). The spatial requirements of a real chain also contribute to the maintenance of short-range interactions (Flory 1969).

However, it is assumed that in concentrated guanidinium chloride solution a "complete" unfolding is achieved which corresponds to that caused by other denaturing agents (Privalov 1979, Creighton 1978). However, using the methods of NMR spectroscopy (Wüthrich 1986) it is also possible to examine the structure and dynamics of individual groups in the denatured state. This appears as a large number of significantly different "polymorphic" conformers in rapid equilibrium (Dobson et al. 1985). The examination of protein mutants strongly indicates that the compactness of the denatured state as well as its energy can be strongly influenced by individual mutations (Shortle 1992).

Using the two state model the thermodynamic equilibrium constant K can be defined:

$$F \rightleftharpoons U \quad (1)$$

$$K_u = \frac{[U]}{[F]} \quad (2)$$

The free enthalpy of unfolding can be derived therefrom as:

$$\Delta G_u = -RT \ln K_u \quad (3)$$

The ratio [U]/[F] can be determined with numerous spectroscopic measurement methods which detect a difference in the properties of the native and unfolded state e.g. circular dichroism, UV absorption or fluorescence spectroscopy. The latter method is the most sensitive and one requires the least amount of protein. A measured signal I is thus composed of the addition of components of the folded ($I_f$) and unfolded ($I_u$):

$$I = I_u + I_f$$

These are proportional to the respective equilibrium concentrations [F] and [U]. Using $c_f$ and $c_u$ as proportionality constants which are given by the substance-specific spectroscopic properties of the two states one obtains:

$$I = C_f[F] + C_u[U] \quad (4)$$

Using the balance for the amount of substance ([P]: protein concentration)

$$[P] = [F] + [U] \quad (5)$$

one obtains by dividing (4) and (5) after transformation and taking into consideration $c_f[P] = I_f o$ and $c_u[P] = I_u o$ which represent the signal intensities of the completely folded and unfolded state:

$$\frac{[U]}{[F]} = \frac{I - I_f^o}{I^o - I} \quad (6)$$

It may occur that the signal intensities of the completely folded and unfolded state depend on the concentration of the denaturing agent. This can be taken into account in a good approximation by a linear dependency. In the case of the $V_L$ domains of the present document this only applies to the unfolded state and is taken into account using (7).

$$I_u^o([GdmHCl]) = I_u^o - a \cdot [GdmHCl] \quad (7)$$

When a protein is unfolded by a denaturing agent such as guanidinium chloride the stability of the protein is reduced with increasing concentrations of denaturing agent and in other words $\Delta G_u$ becomes smaller. In analysing denaturing curves for proteins which exhibit a two state behaviour it is assumed that there is a linear relationship between the concentration of the denaturing agent and $\Delta G_u$ (Pace 1986, Alonso and Dill 1991).

$$\Delta G_u = \Delta G_u^o - m \cdot [D] \quad (8)$$

By using (3) and (6) $\Delta G_u$ can be calculated in the concentration range of the denaturing agent in which the folded as well as the unfolded form is present in detectable concentrations. The free enthalpy of unfolding in the absence of the denaturing agent is then obtained by linear extrapolation to zero molar denaturing agent whereby the applicability of (8) is taken as the basis.

A second method of analysis is to derive an expression for the signal intensity in relation to the parameters (9) using (2), (3), (6), (7) and (8) and then to obtain this by matching the theoretical shape of the curve to the measured values according to the principle of least square errors.

$$I = I_u^o - a \cdot [GdmHCl] + \frac{I_f^o - I_u^o + a \cdot [GdmHCl]}{1 + e^{\frac{m \cdot [GdmHCl] - \Delta G_u^o}{RT}}} \quad (9)$$

The following quantities occur as parameters: $I_u^o$, $I_f^o$, $\Delta G_u^o$, a and m.

In order to establish denaturing curves of the $V_L$ mutants the fluorescence is used as a measurement parameter. The fluorescence of the $V_L$ protein is mainly attributable to the single tryptophan residue 35 which is packed in the inside of the protein against the central disulfide bridge. In the course of unfolding the trpytophan residue comes into a more hydrophilic environment and the interaction with the disulfide bridge is lost. The very low fluorescence of the folded protein is due to the fluorescence quenching effect of the disulfide bridge (Cowgill 1967).

FIG. 2 shows the fluorescence spectra in the folded and unfolded state (2 mM protein in PBS with 0 M and 5 M GdmHCl 20° C.) as well as the difference spectrum of both. In the course of unfolding the protein fluorescence with a maximum at 350 nm increases by about a factor of 16. Thus in the present case the fluorescence proves to be an ideal measurement parameter since it changes considerably when the protein unfolds. FIG. 3 shows an excitation spectrum, the fluorescence at 350 is determined in relation to the excitation wavelength. A pronounced maximum at 280 nm can be seen.

PBS 4 mM $KH_2PO_4$ 16 mM $Na_2HPO_4$ 115 mM NaCl the pH value is 7.4

Several measurements were usually carried out, the data were obtained by averaging the values standardized according to (10) (from (5), (6) and (7)).

$$\frac{[U]}{[P]} = \frac{I - I_f^o}{I_u^o - a \cdot [GdmHCl] - I_f^o} \quad (10)$$

From the parameters obtained it is possible to calculate the concentration at which half the protein is present in an unfolded state, the denaturation mid-point $[GdMHCl]_{1/2}$. In this case $DG_U = 0$. From (8) one obtains (11).

$$[GdmHCl]_{1/2} = \frac{\Delta G_u^o}{m} \quad (11)$$

The parameters of the individual measurements are summarized in table 7.

TABLE 7

Comparison between prediction and experiment for stabilizing point mutations

| Domain | $f_{WT}$ | $f_{mut}$ | $\Delta G^P$fold (kJ mol$^{-1}$) | Experiments | Prediction |
|---|---|---|---|---|---|
| WT | | | −13.5 | | |
| Ala15Leu | 0.082 | 0.411 | −19.2 | ++ | ++ |
| Asn90Gln | 0.047 | 0.892 | −17.9 | ++ | ++ |
| Phe32Tyr | 0.034 | 0.799 | −15.1 | + | ++ |
| Leu106Ile | 0.298 | 0.684 | −15.0 | + | + |
| Thr63Ser | 0.148 | 0.823 | −14.7 | + | ++ |

TABLE 7-continued

Comparison between prediction and experiment
for stabilizing point mutations

| Domain | $f_{WT}$ | $f_{mut}$ | $\Delta G^P fold$ (kJ mol$^{-1}$) | Experiments | Prediction |
|---|---|---|---|---|---|
| Met21Ile | 0.278 | 0.590 | −14.5 | + | + |
| Met21Leu | 0.278 | 0.103 | −12.2 | − | − |

In the expression of the proteins it was also surprisingly observed that the yield increased in comparison to the wild-type to about nine to 26 milligrams in the case of more stable mutants.

7. LIST OF REFERENCES

Alonso, D. O. V., Dill, K. A. (1991). Solvent Denaturation and Stabilization of Globular Proteins. *Biochemistry* 30, 5974–5985

Birnboim, C. Doly, J. (1979). Rapid alkaline extraction procedure for screening recombinant plasmid DNA. *Nucleic Acids. Res.* 7, 1513–1523

Cowgill, R. W. (1967). Fluorescence Quenching by Disulfide and Sulfhydryl Groups. *Biochimica et Biophysica acta* 140, 37–44

Creighton, T. E. (1978). Experimental Studies of Protein Folding and Unfolding. *Prog. Biophys. molec. Biol.* 33, 231–297

Devereux et al., Nucleic Acids Res. 12 (1984), 387–395

Dobson, C. M. Evans, P. A., Fox, R. O. (1985). In: *Structure and Motion. Membranes Nucleic Acids and Proteins,* Adenine, Guilderland, New York, 265–276

Flory, P. (1969). *Statistical Mechanics of Chain Molecules,* Wiley, New York, 432 ff.

Frisch C. et al., Biol. Chem. Hoppe-Seyler 375 (1994) 353–356

Geisselsoder, J., Witney, F., Yuckenberg, P. (1987). Efficient site-dircted in vitro mutagenesis. *Biotechniques* 5, 786–791

Gellert, W. (Publ.) (1984). Kleine Enzyklopädie Mathematik, 2. Auflage, Verlag Harri Deutsch, Thun Frankfurt/M., 668 ff.

Gilbert, H. F. (1990). Molecular and cellular aspects of thiol-disulfide exchange. *Adv. Enzymol.* 63, 69–172

Glockshuber, R. (1989). Das F$_v$-Fragment des Phosphorylcholin bindenden Antikörpers McPC603: Expression in *Escherichia coli* und Charakterisierung. Dissertation, Fakultät für Chemie und Pharmazie of the Ludwig-Maximilians-University, Munich Hanahan, D. (1983). Studies of transformation of *Escherichia coli* with plasmids. *J. Mol. Biol.* 166, 557–579

Hochuli, E., Bannworth, W., Döbeli, H., Gentz, R., Süber, D. (1988). Genetic approach to facilitate purification of recombinant proteins with a novel metal chelate adsorbent. *Bio/Technology* 6, 1321–1325

Kaplan, B. E. (1985). The automated synthesis of oligodeoxyribonucleotides. *Trends Biotechnol.* 3, 253–256

Kunkel, T. A. Roberts, J. D., Zakow, R. A. (1987). Rapid and efficient site-specific mutagenesis without phenotypic selection. *Methods Enzymol.*154, 367–382

Maniatis, T. Fritsch, E. F., Sambrook, J. (1982). *Molecular cloning: A laboratory manual.* Cold Spring Harbor Laboratory, New York Morrison, S. L. et al., Ann. Rev. Immunol. 2 (1984) 239–256

Pace, C. N. (1986). Determination and Analysis of Urea and Guanidine Hydrochloride Denaturation Curves. *Methods Enzymol.* 131, 266

Privalov, P. L., Gill, S. J. (1989). The hydrophobic effect: a reappraisal. *Pure & Appl. Chem.* 61, 1097–1104

Shortle, D. (1992). Mutational studies of protein structures and their stabilities. *Q. Rev. Bioph.* 25, 205–250

Skerra, A., Plückthun, A. (1988). Assembly of functional F$_v$ fragments in *Escherichia coli. Science* 240, 1038–1041

Tanford, C. (1970). Protein Denaturation. Part C. Theoretical Models for the Mechanism of Denaturation. *Adv. Protein Chem.* 24, 1–95

Vieira, J. Messing, J. (1987). Production of single-stranded plasmid DNA. Methods. *Enzymol.* 153, 3–11

Wüthrich, K. (1986). *NMR of Proteins and Nucleic Acids,* Wiley, New York, 293 ff.

Yanisch-Perron, C., Vieira, J. Messing, J. (1985). Improved M13 phage cloning vectors and host strains: Nucleotide sequences of the M13mp18 and pUC19 vectors. *Gene* 33, 103–119

Frisch, C. et. al., Biol. Chem. Hoppe-Seyler 375 375 (1994) 353–356

Rollence, M. L., Filpula, D., Pantoliano, M. W. & Bryan P. N. Crit. Rev. Biotechnol. 8, 217–224 (1988)

Chen, L. H. & Baldwin, T. O. Biochemistry 28, 2684–2689 (1989)

Turner, S. L., Ford, G. C., Mountain, A. & Moir, A. Prot. Eng. 5, 535–541 (1992)

Risse, B., Stempfer, G., Rudolph, R., Schumacher, G., & Jaenicke, R. Protein Science 1, 1710–1718 (1992).

Arase, A., Yomo, T., Urabe, I., Hata, Y., Katsube, Y. & Okada, H. FEBS lett., 316, 123–127 (1993).

Kabat, E. A., Wu, T. T., Perry, H. M., Gottesman, K. S. & Foeller, C. Sequences of Proteins of Immunological Interest, 5th ed. US Dept. Health and Human Services, Bethesda, Md. (1991)

Tonegawa, S. Nature 302, 575–581 (1983)

Berek, C. & Milstein, C., Immunol.Rev. 105, 5–26 (1988)

French, D. L., Laskov, R. & Scharff, M. D. Science, 244, 1152–1157 (1989)

Berek, C. & Ziegner, M. Immunol. Today 14, 400–404 (1993)

Jung, S. H. et al., Proteins: Structure Function and Genetics 19 (1994) 35–47

Glockshuber, R. et al., Biochemistry 29 (1990) 1362–1367

Lindner, P. et al., Methods: A comparison to Methods of Enzymology 4 (1992) 41–56

TABLE 1

Variable domains of the heavy chain of humans
Determined consensus sequence (SEQ ID NO: 1)
Table 1

```
1  EVQLVESGGGLVKPGGSLRLSCAASGFTFESSYAMS - - - WVRQA
41 PGKGLEWVGWIY - - - NGGDTYYADSVKGRFTISRDTSKNTLYL
81 QMNSLRAEDTAVYYCARGGGGGY - - - FDYWGQGTLVTVSS
```
(SEQ ID NO:1 shows the consensus sequence without inserts)

| Position | Type and frequency |
|---|---|
| 1: | E:0.505 Q:0.460 |
| 2: | V:0.939 |
| 3: | Q:0.920 |
| 4: | L:0.997 |
| 5: | V:0.680 Q:0.177 L:0.106 |
| 6: | E:0.638 Q:0.333 |
| 7: | S:0.930 |

TABLE 1-continued

Variable domains of the heavy chain of humans
Determined consensus sequence (SEQ ID NO: 1)
Table 1

1 EVQLVESGGGLVKPGGSLRLSCAASGFTFESSYAMS - - - WVRQA
41 PGKGLEWVGWIY - - - NGGDTYYADSVKGRFTISRDTSKNTLYL
81 QMNSLRAEDTAVYYCARGGGGGY - - - FDYWGQGTLVTVSS
(SEQ ID NO:1 shows the consensus sequence without inserts)

| Position | Type and frequency |
|---|---|
| 8: | G:1.000 |
| 9: | G:0.566 A:0.215 P:0.177 |
| 10: | G:0.609 E:0.246 |
| 11: | L:0.637 V:0.336 |
| 12: | V:0.701 K:0.221 |
| 13: | K:0.455 Q:0.455 |
| 14: | P:0.964 |
| 15: | G:0.796 S:0.177 |
| 16: | G:0.357 R:0.189 Q:0.124 E:0.116 A:0.116 |
| 17: | S:0.803 T:0.179 |
| 18: | L:0.794 V:0.188 |
| 19: | R:0.574 K:0.230 S:0.164 |
| 20: | L:0.730 V:0.217 |
| 21: | S:0.786 T:0.214 |
| 22: | C:1.000 |
| 23: | A:0.506 K:0.228 T:0.132 |
| 24: | A:0.655 V:0.174 |
| 25: | S:0.977 |
| 26: | G:0.985 |
| 27: | F:0.578 Y:0.161 G:0.147 |
| 28: | T:0.585 S:0.266 |
| 29: | F:0.804 |
| 30: | S:0.761 T:0.110 |
| 31: | S:0.389 D:0.167 T:0.160 |
| 32: | Y:0.535 S:0.124 |
| 33: | A:0.292 Y:0.168 W:0.127 |
| 34: | M:0.598 T:0.183 |
| 35: | S:0.310 H:0.272 N:0.112 |
| 35a: | -:0.897 |
| 35b: | -:0.922 |
| 36: | W:1.000 |
| 37: | V:0.784 I:0.151 |
| 38: | R:1.000 |
| 39: | Q:0.994 |
| 40: | A:0.648 P:0.162 |
| 41: | P:0.923 |
| 42: | G:0.969 |
| 43: | K:0.729 Q:0.156 R:0.104 |
| 44: | G:0.909 |
| 45: | L:0.959 |
| 46: | E:0.972 |
| 47: | W:0.996 |
| 48: | V:0.566 M:0.196 I:0.150 |
| 49: | G:0.510 S:0.243 A:0.197 |
| 50: | W:0.199 V:0.113 |
| 51: | I:0.807 |
| 52: | Y:0.211 S:0.167 N:0.115 G:0.107 |
| 52a: | -:0.198 P:0.159 Y:0.128 G:0.113 |
| 52b: | -:0.897 |
| 52c: | -:0.927 |
| 53: | N:0.170 D:0.166 S:0.134 G:0.125 |
| 54: | G:0.402 S:0.204 |
| 55: | G:0.476 S:0.269 |
| 56: | D:0.198 S:0.183 T:0.158 N:0.143 |
| 57: | T:0.465 K:0.105 |
| 58: | Y:0.304 N:0.186 H:0.114 |
| 59: | Y:0.894 |
| 60: | A:0.656 N:0.129 |
| 61: | D:0.394 P:0.205 Q:0.138 |
| 62: | S:0.714 K:0.122 |
| 63: | V:0.590 F:0.219 L:0.154 |
| 64: | K:0.554 Q:0.237 |
| 65: | G:0.785 S:0.148 |
| 66: | R:0.926 |
| 67: | F:0.602 V:0.348 |
| 68: | T:0.878 |
| 69: | I:0.806 M:0.111 |
| 70: | S:0.789 T:0.130 |
| 71: | R:0.597 V:0.150 |
| 72: | D:0.815 N:0.152 |
| 73: | T:0.301 N:0.284 D:0.253 |
| 74: | S:0.890 A:0.103 |
| 75: | K:0.643 |
| 76: | N:0.672 S:0.221 |
| 77: | T:0.659 Q:0.211 |
| 78: | L:0.462 A:0.252 F:0.179 |
| 79: | Y:0.710 S:0.192 |
| 80: | L:0.822 M:0.169 |
| 81: | Q:0.573 E:0.198 |
| 82: | M:0.548 L:0.344 |
| 82a: | N:0.399 S:0.300 |
| 82b: | S:0.797 |
| 82c: | L:0.753 V:0.202 |
| 83: | R:0.542 T:0.196 K:0.131 |
| 84: | A:0.485 P:0.191 S:0.134 |
| 85: | E:0.644 A:0.155 D:0.127 |
| 86: | D:0.972 |
| 87: | T:0.940 |
| 88: | A:0.956 |
| 89: | V:0.765 |
| 90: | Y:0.992 |
| 91: | Y:0.947 |
| 92: | C:0.998 |
| 93: | A:0.891 |
| 94: | R:0.681 K:0.158 |
| 95: | G:0.179 D:0.152 E:0.119 V:0.100 |
| 96: | G:0.118 P:0.101 |
| 97: | G:0.168 S:0.122 |
| 98: | G:0.132 Y:0.103 |
| 99: | G:0.240 A:0.111 |
| 100: | Y:0.139 S:0.127 -:0.127 G:0.120 |
| 100a: | -:0.276 S:0.160 |
| 100b: | -:0.379 S:0.107 G:0.101 |
| 100c: | -:0.429 Y:0.110 |
| 100d: | -:0.567 |
| 100e: | -:0.645 Y:0.129 |
| 100f: | -:0.728 Y:0.107 |
| 100g: | -:0.758 V:0.114 |
| 100h: | -:0.825 |
| 100i: | -:0.868 |
| 100j: | -:0.481 Y:0.147 |
| 100k: | F:0.475 -:0.176 M:0.160 L:0.100 |
| 101: | D:0.755 |
| 102: | Y:0.442 V:0.239 |
| 103: | W:0.967 |
| 104: | G:0.953 |
| 105: | Q:0.823 |
| 106: | G:1.000 |
| 107: | T:0.887 |
| 108: | L:0.659 T:0.194 |
| 109: | V:0.986 |
| 110: | T:0.916 |
| 111: | V:0.969 |
| 112: | S:0.980 |
| 113: | S:0.930 |

TABLE 2

Variable domains of the heavy chain of the mouse
Determined consensus sequence (SEQ ID NO: 2)
1 EVQLQQSGGELVKPGASVKLSCKASGYTFTSYYMH - - - WVKQR
41 PGKGLEWIGRINP - - - GSGGTNYNEKFKGKATLTRDKSSSTAYL
81 QLSSLTSEDSAVYYCARGGYY - - -YFDYWGQGTTVTVSS
(SEQ ID NO:2 shows the consensus sequence without inserts)

| Position | Type and frequency |
|---|---|
| 1: | E:0.504 Q:0.409 |
| 2: | V:0.965 |
| 3: | Q:0.756 K:0.186 |
| 4: | L:0.968 |
| 5: | Q:0.575 V:0.227 |
| 6: | Q:0.563 E:0.434 |
| 7: | S:0.818 P:0.122 |
| 8: | G:0.976 |
| 9: | G:0.314 P:0.311 A:0.246 T:0.107 |
| 10: | E:0.560 G:0.353 |
| 11: | L:0.951 |
| 12: | V:0.810 |
| 13: | K:0.526 Q:0.248 R:0.118 |
| 14: | P:0.895 |
| 15: | G:0.883 |
| 16: | A:0.383 G:0.314 |
| 17: | S:0.940 |
| 18: | V:0.599 L:0.290 |
| 19: | K:0.738 S:0.100 |
| 20: | L:0.569 I:0.245 M:0.173 |
| 21: | S:0.915 |
| 22: | C:1.000 |
| 23: | K:0.528 A:0.222 T:0.121 |
| 24: | A:0.779 |
| 25: | S:0.912 |
| 26: | G:0.988 |
| 27: | Y:0.591 F:0.380 |
| 28: | T:0.671 S:0.171 |
| 29: | F:0.858 |
| 30: | T:0.578 S:0.323 |
| 31: | S:0.351 D:0.276 N:0.122 |
| 32: | Y:0.723 |
| 33: | Y:0.312 W:0.298 G:0.163 |
| 34: | M:0.664 I:0.199 |
| 35: | H:0.300 N:0.283 S:0.181 |
| 35a: | -:0.971 |
| 35b: | -:0.998 |
| 36: | W:0.997 |
| 37: | V:0.909 |
| 38: | K:0.550 R:0.434 |
| 39: | Q:0.945 |
| 40: | R:0.384 S:0.170 A:0.143 T:0.105 |
| 41: | P:0.866 |
| 42: | G:0.750 E:0.195 |
| 43: | K:0.525 Q:0.321 |
| 44: | G:0.671 R:0.108 S:0.102 |
| 45: | L:0.981 |
| 46: | E:0.930 |
| 47: | W:0.944 |
| 48: | I:0.647 V:0.176 L:0.102 |
| 49: | G:0.742 A:0.250 |
| 50: | R:0.196 Y:0.157 E:0.103 |
| 51: | I:0.921 |
| 52: | N:0.295 Y:0.8585 S:0.147 D:0.116 R:0.101 |
| 52a: | P:0.550 S:0.148 |
| 52b: | -:0.893 K:0.104 |
| 52c: | -:0.891 |
| 53: | G:0.321 N:0.190 Y:0.162 S:0.102 |
| 54: | S:0.310 N:0.309 G:0.222 |
| 55: | G:0.568 S:0.153 Y:0.107 |
| 56: | G:0.162 Y:0.158 S:0.149 T:0.126 N:0.117 |
| 57: | T:0.763 I:0.115 |
| 58: | N:0.295 Y:0.183 K:0.161 |
| 59: | Y:0.956 |
| 60: | N:0.536 A:0.181 |
| 61: | E:0.294 Q:0.197 D:0.184 P:0.150 |
| 62: | K:0.508 S:0.269 |
| 63: | F:0.607 V:0.221 L:0.131 |
| 64: | K:0.809 |
| 65: | G:0.596 D:0.174 S:0.166 |
| 66: | K:0.532 R:0.466 |
| 67: | A:0.516 F:0.341 |
| 68: | T:0.773 |
| 69: | L:0.437 I:0.417 |
| 70: | T:0.590 S:0.373 |
| 71: | R:0.339 V:0.306 A:0.230 |
| 72: | D:0.895 |
| 73: | K:0.366 N:0.258 T:0.238 |
| 74: | S:0.764 A:0.123 |
| 75: | S:0.539 K:0.254 |
| 76: | S:0.585 N:0.334 |
| 77: | T:0.772 |
| 78: | A:0.514 L:0.269 V:0.168 |
| 79: | Y:0.868 F:0.108 |
| 80: | L:0.481 M:0.475 |
| 81: | Q:0.742 E:0.137 |
| 82: | L:0.589 M:0.342 |
| 82a: | S:0.525 N:0.286 |
| 82b: | S:0.710 N:0.109 |
| 82c: | L:0.891 V:0.101 |
| 83: | T:0.587 R:0.231 K:0.104 |
| 84: | S:0.736 |
| 85: | E:0.876 |
| 86: | D:0.981 |
| 87: | S:0.513 T:0.428 |
| 88: | A:0.941 |
| 89: | V:0.542 T:0.150 M:0.126 I:0.104 |
| 90: | Y:0.980 |
| 91: | Y:0.770 F:0.227 |
| 92: | C:0.997 |
| 93: | A:0.725 T:0.127 |
| 94: | R:0.821 |
| 95: | G:0.174 D:0.158 Y:0.125 |
| 96: | G:0.205 Y:0.150 |
| 97: | Y:0.242 G:0.181 |
| 98: | Y:0.249 -:0.208 G:0.149 |
| 99: | -:0.310 G:0.181 S:0.105 |
| 100: | -:0.484 S:0.110 G:0.108 |
| 100a: | -:0.612 |
| 100b: | -:0.768 |
| 100c: | -:0.867 |
| 100d: | -:0.910 |
| 100e: | -:0.974 |
| 100f: | -:0.986 |
| 100g: | -:0.992 |
| 100h: | -:0.997 |
| 100i: | -:1.000 |
| 100j: | Y:0.324 -:0.276 A:0.177 W:0.101 |
| 100k: | F:0.590 M:0.187 -:0.108 |
| 101: | D:0.668 A:0.233 |
| 102: | Y:0.774 V:0.152 |
| 103: | W:0.986 |
| 104: | G:0.985 |
| 105: | Q:0.834 |
| 106: | G:0.993 |
| 107: | T:0.973 |
| 108: | T:0.475 L:0.283 S:0.226 |
| 109: | V:0.695 L:0.294 |
| 110: | T:0.960 |
| 111: | V:0.987 |
| 112: | S:0.984 |
| 113: | S:0.753 A:0.233 |

TABLE 3

Variable domains of the light chain of the kappa type of humans
Determined consensus sequence (SEQ IS NO: 3)
1 DIQMTQSPSSLSASVGDRVTTTCRASQSISS - - - YLAWYQQKPGKAPKLLIYD
51 ASNLESGVPSRFSGSGSGTDFTLTISSLQPEDFATYYCQQYYSLP - - - YTFGQ
101 GTKVEI-KRT
(SEQ ID NO:3 shows the consensus sequence without inserts)

| Position | Type and frequency |
|---|---|
| 1: | D:0.858 E:0.133 |
| 2: | I:0.933 |
| 3: | Q:0.746 V:0.237 |
| 4: | M:0.754 L:0.240 |
| 5: | T:0.999 |
| 6: | Q:1.000 |
| 7: | S:0.985 |
| 8: | P:1.000 |
| 9: | S:0.750 |
| 10: | S:0.630 T:0.339 |
| 11: | L:0.965 |
| 12: | S:0.885 |
| 13: | A:0.683 V:0.206 L:0.111 |
| 14: | S:0.927 |
| 15: | V:0.741 P:0.188 |
| 16: | G:1.000 |
| 17: | D:0.763 E:0.227 |
| 18: | R:0.875 |
| 19: | V:0.742 A:0.224 |
| 20: | T:0.915 |
| 21: | I:0.758 L:0.203 |
| 22: | T:0.693 S:0.193 |
| 23: | C:1.000 |
| 24: | R:0.678 Q:0.146 |
| 25: | A:0.801 S:0.145 |
| 26: | S:0.876 |
| 27: | Q:0.914 |
| 28: | S:0.569 T:0.129 |
| 29: | I:0.435 V:0.390 L:0.101 |
| 30: | S:0.374 L:0.165 V:0.107 N:0.100 |
| 31: | S:0.244 N:0.214 K:0.152 Y:0.109 |
| 31a: | -:0.717 S:0.210 |
| 31b: | -:0.812 |
| 31c: | -:0.811 |
| 31d: | -:0.811 N:0.113 |
| 31e: | -:0.855 |
| 31f: | -:0.936 |
| 32: | Y:0.544 W:0.151 |
| 33: | L:0.930 |
| 34: | A:0.477 N:0.355 |
| 35: | W:1.000 |
| 36: | Y:0.909 |
| 37: | Q:0.907 |
| 38: | Q:0.985 |
| 39: | K:0.909 |
| 40: | P:0.985 |
| 41: | G:0.913 |
| 42: | K:0.669 Q:0.289 |
| 43: | A:0.871 |
| 44: | P:0.998 |
| 45: | K:0.576 R:0.189 N:0.105 |
| 46: | L:0.786 |
| 47: | L:0.996 |
| 48: | I:0.975 |
| 49: | Y:0.912 |
| 50: | D:0.263 A:0.255 G:0.176 |
| 51: | A:0.772 V:0.113 |
| 52: | S:0.951 |
| 53: | N:0.389 S:0.292 T:0.252 |
| 54: | L:0.693 R:0.307 |
| 55: | E:0.335 Q:0.219 A:0.168 |
| 56: | S:0.490 T:0.333 |
| 57: | G:0.981 |
| 58: | V:0.788 I:0.183 |
| 59: | P:0.992 |
| 60: | S:0.745 D:0.160 |
| 61: | R:0.944 |
| 62: | F:0.989 |

TABLE 3-continued

Variable domains of the light chain of the kappa type of
humans
Determined consensus sequence (SEQ IS NO: 3)
1 DIQMTQSPSSLSASVGDRVTITCRASQSISS - - - YLAWYQQKPGKAPKLLIYD
51 ASNLESGVPSRFSGSGSGTDFTLTISSLQPEDFATYYCQQYYSLP - - - YTFGQ
101 GTKVEI-KRT
(SEQ ID NO:3 shows the consensus sequence without
inserts)

| Position | Type and frequency |
|---|---|
| 63: | S:0.889 |
| 64: | G:0.992 |
| 65: | S:0.860 |
| 66: | G:0.882 |
| 67: | S:0.980 |
| 68: | G:0.968 |
| 69: | T:0.954 |
| 70: | D:0.782 E:0.180 |
| 71: | F:0.977 |
| 72: | T:0.898 |
| 73: | L:0.766 F:0.223 |
| 74: | T:0.930 |
| 75: | I:0.953 |
| 76: | S:0.870 |
| 77: | S:0.669 R:0.136 G:0.131 |
| 78: | L:0.907 |
| 79: | Q:0.753 E:0.164 |
| 80: | P:0.817 |
| 81: | E:0.803 D:0.177 |
| 82: | D:0.957 |
| 83: | F:0.656 V:0.143 T:0.140 |
| 84: | A:0.945 |
| 85: | T:0.598 V:0.283 |
| 86: | Y:0.989 |
| 87: | Y:0.919 |
| 88: | C:1.000 |
| 89: | Q:0.830 |
| 90: | Q:0.950 |
| 91: | Y:0.565 S:0.159 |
| 92: | Y:0.276 N:0.204 D:0.169 S:0.102 |
| 93: | S:0.327 T:0.199 N:0.193 |
| 94: | L:0.254 S:0.154 Y:0.150 F:0.121 T:0.116 |
| 95: | P:0.815 |
| 95a: | -:0.908 |
| 95b: | -:1.000 |
| 95c: | -:1.000 |
| 95d: | -:1.000 |
| 95e: | -:1.000 |
| 95f: | -:1.000 |
| 96: | Y:0.197 R:0.177 W:0.130 |
| 97: | T:0.897 |
| 98: | F:0.988 |
| 99: | G:1.000 |
| 100: | Q:0.612 G:0.275 |
| 101: | G:1.000 |
| 102: | T:0.953 |
| 103: | K:0.810 R:0.116 |
| 104: | V:0.714 L:0.240 |
| 105: | E:0.699 D:0.207 |
| 106: | I:0.717 |
| 106a: | -:1.000 |
| 107: | K:0.902 |
| 108: | R:0.959 |
| 109: | T:1.000 |

TABLE 4

Variable domains of the light chain of the kappa type of
the mouse
Determined consensus sequence (SEQ ID NO: 4
1 DIVMTQSPASLSASLGERVTITCRASQSVSS - - - YLHWYQQKPGQSPKLLIYR
52 ASNLASGVPDRFSGSGSGTDFTLTISSVEAEDLATYYCQQSNSYP - - - YTFGG
101 GTKLEI - - - KR
(SEQ ID NO:4 shows the consensus sequence without
inserts)

| Position | Type and frequency |
|---|---|
| 1: | D:0.707 E:0.106 Q:0.104 |
| 2: | I:0.813 V:0.121 |
| 3: | V:0.653 Q:0.223 |
| 4: | M:0.520 L:0.424 |
| 5: | T:0.878 |
| 6: | Q:0.995 |
| 7: | S:0.808 T:0.152 |
| 8: | P:0.871 |
| 9: | A:0.383 S:0.313 K:0.115 |
| 10: | S:0.571 I:0.177 |
| 11: | L:0.578 M:0.322 |
| 12: | S:0.476 A:0.257 P:0.117 |
| 13: | A:0.482 V:0.393 |
| 14: | S:0.874 |
| 15: | L:0.464 P:0.273 V:0.133 |
| 16: | G:0.977 |
| 17: | E:0.462 D:0.313 Q:0.188 |
| 18: | R:0.447 K:0.282 |
| 19: | V:0.693 A:0.192 I:0.103 |
| 20: | T:0.708 S:0.253 |
| 21: | I:0.607 M:0.224 L:0.122 |
| 22: | T:0.487 S:0.432 |
| 23: | C:0.984 |
| 24: | R:0.476 K:0.253 S:0.161 |
| 25: | A:0.812 S:0.166 |
| 26: | S:0.974 |
| 27: | Q:0.524 S:0.231 E:0.133 |
| 28: | S:0.623 D:0.157 N:0.118 |
| 29: | V:0.411 T:0.383 L:0.176 |
| 30: | S:0.468 G:0.129 |
| 31: | S:0.227 N:0.192 T:0.158 -:0.111 |
| 31a: | -:0.569 S:0.256 |
| 31b: | -:0.685 G:0.141 |
| 31c: | -:0.685 G:G.102 |
| 31d: | -:0.690 S:0.112 |
| 31e: | -:0.821 T:0.103 |
| 31f: | -:0.924 |
| 32: | Y:0.652 N:0.122 |
| 33: | L:0.603 M:0.231 V:0.114 |
| 34: | H:0.330 A:0.227 N:0.155 |
| 35: | W:0.989 |
| 36: | Y:0.790 F:0.126 |
| 37: | Q:0.893 L:0.102 |
| 38: | Q:0.926 |
| 39: | K:0.879 |
| 40: | P:0.808 S:0.134 |
| 41: | G:0.773 |
| 42: | Q:0.450 K:0.151 G:0.105 |
| 43: | S:0.641 P:0.154 T:0.114 |
| 44: | P:0.888 |
| 45: | K:0.810 |
| 46: | L:0.802 |
| 47: | L:0.814 W:0.171 |
| 48: | I:0.938 |
| 49: | Y:0.880 |
| 50: | R:0.186 Y:0.164 S:0.147 G:0.137 A:0.102 |
| 51: | A:0.507 T:0.296 |
| 52: | S:0.893 |
| 53: | N:0.469 T:0.146 |
| 54: | L:0.630 R:0.262 |
| 55: | A:0.322 E:0.182 Y:0.123 |
| 56: | S:0.687 T:0.140 |
| 57: | G:0.997 |
| 58: | V:0.864 I:0.132 |
| 59: | P:0.961 |
| 60: | D:0.354 S:0.279 A:0.262 |
| 61: | R:0.976 |
| 62: | F:0.997 |

TABLE 4-continued

Variable domains of the light chain of the kappa type of
the mouse
Determined consensus sequence (SEQ ID NO: 4)
1 DIVMTQSPASLSASLGERVTITCRASQSVSS - - - YLHWYQQKPGQSPKLLIYR
52 ASNLASGVPDRFSGSGSGTDFTLTISSVEAEDLATYYCQQSNSYP - - - YTFGG
101 GTKLEI - - - KR
(SEQ ID NO:4 shows the consensus sequence without
inserts)

| Position | Type and frequency |
|---|---|
| 63: | S:0.776 T:0.192 |
| 64: | G:0.992 |
| 65: | S:0.981 |
| 66: | G:0.955 |
| 67: | S:0.969 |
| 68: | G:0.896 |
| 69: | T:0.862 |
| 70: | D:0.675 S:0.226 |
| 71: | F:0.618 Y:0.373 |
| 72: | T:0.554 S:0.434 |
| 73: | L:0.901 |
| 74: | T:0.702 K:0.111 |
| 75: | I:0.977 |
| 76: | S:0.716 N:0.107 |
| 77: | S:0.567 P:0.142 R:0.127 |
| 78: | V:0.483 L:0.268 M:0.232 |
| 79: | E:0.667 Q:0.284 |
| 80: | A:0.479 S:0.124 P:0.115 E:0.106 |
| 81: | E:0.878 D:0.115 |
| 82: | D:0.976 |
| 83: | L:0.261 A:0.223 F:0.149 T:0.108 V:0.108 |
| 84: | A:0.764 G:0.170 |
| 85: | T:0.446 V:0.216 D:0.120 |
| 86: | Y:0.995 |
| 87: | Y:0.712 F:0.259 |
| 88: | C:0.999 |
| 89: | Q:0.669 L:0.131 |
| 90: | Q:0.905 |
| 91: | S:0.196 G:0.196 H:0.193 Y:0.117 W:0.100 |
| 92: | N:0.224 S:0.223 Y:0.169 |
| 93: | S:0.395 E:0.199 |
| 94: | Y:0.285 L:0.114 S:0.101 |
| 95: | P:0.938 |
| 95a: | -:0.957 |
| 95b: | -:0.990 |
| 95c: | -:1.000 |
| 95d: | -:1.000 |
| 95e: | -:1.000 |
| 95f: | -:1.000 |
| 96: | Y:0.263 L:0.255 W:0.172 R:0.114 |
| 97: | T:0.992 |
| 98: | F:1.000 |
| 99: | G:0.996 |
| 100: | G:0.631 A:0.244 S:0.114 |
| 101: | G:0.997 |
| 102: | T:1.000 |
| 103: | K:0.974 |
| 104: | L:0.995 |
| 105: | E:0.996 |
| 106: | I:0.763 |
| 106a: | -:1.000 |
| 107: | K:0.958 |
| 108: | R:1.000 |

TABLE 5

Variable domains of the light chain of the lambda type of humans
Determined consensus sequence (SEQ ID NO: 5)
1 QSELTQPPS-VSVSPGQTVTISCSGDSLGIG - - - YVSWYQQKPGQAPKLVIYD
51 DNKRPSGIPDRFSGSKSGHTASLTISGLQAEDEADYYCQSWDSSS - - - VVFGG
101 GTKLTVLGQP
(SEQ ID NO:5 shows the consensus sequence without inserts)

| Position | Type and frequency |
|---|---|
| 1: | Q:0.557 S:0.211 |
| 2: | S:0.486 Y:0.392 |
| 3: | E:0.299 A:0.271 V:0.239 |
| 4: | L:0.995 |
| 5: | T:0.920 |
| 6: | Q:1.000 |
| 7: | P:0.865 |
| 8: | P:0.704 A:0.126 |
| 9: | S:0.911 |
| 10: | -:1.000 |
| 11: | V:0.858 |
| 12: | S:0.974 |
| 13: | V:0.410 G:0.345 A:0.129 |
| 14: | S:0.656 A:0.259 |
| 15: | P:0.826 L:0.123 |
| 16: | G:0.960 |
| 17: | Q:0.837 |
| 18: | T:0.544 S:0.291 R:0.111 |
| 19: | V:0.434 A:0.391 I:0.126 |
| 20: | T:0.518 R:0.259 |
| 21: | I:0.888 |
| 22: | S:0.518 T:0.457 |
| 23: | C:1.000 |
| 24: | S:0.471 T:0.243 |
| 25: | G:0.903 |
| 26: | D:0.389 S:0.214 T:0.183 |
| 27: | S:0.380 N:0.123 T:0.100 |
| 28: | L:0.366 S:0.322 |
| 29: | G:0.225 D:0.221 N:0.194 P:0.117 |
| 30: | I:0.264 V:0.230 K:0.102 |
| 31: | G:0.303 K:0.151 A:0.129 |
| 31a: | -:0.449 S:0.133 G:0.114 D:0.113 |
| 31b: | -:0.486 N:0.168 Y:0.147 |
| 31c: | -:0.682 N:0.166 |
| 31d: | -:1.000 |
| 31e: | -:1.000 |
| 31f: | -:1.000 |
| 32: | Y:0.413 S:0.211 F:0.104 H:0.100 |
| 33: | V:0.647 A:0.228 |
| 34: | S:0.429 H:0.126 Y:0.110 |
| 35: | W:0.999 |
| 36: | Y:0.856 |
| 37: | Q:0.946 |
| 38: | Q:0.867 |
| 39: | K:0.275 R:0.229 H:0.215 L:0.132 |
| 40: | P:0.921 |
| 41: | G:0.846 |
| 42: | Q:0.453 K:0.224 T:0.156 |
| 43: | A:0.770 S:0.171 |
| 44: | P:0.999 |
| 45: | K:0.400 V:0.319 L:0.111 |
| 46: | L:0.777 |
| 47: | V:0.542 L:0.306 I:0.103 |
| 48: | I:0.822 V:0.131 |
| 49: | Y:0.824 F:0.123 |
| 50: | D:0.284 E:0.254 |
| 51: | D:0.338 V:0.194 N:0.173 |
| 52: | N:0.386 S:0.260 T:0.191 |
| 53: | K:0.255 Q:0.149 N:0.147 D:0.120 |
| 54: | R:0.950 |
| 55: | P:0.905 |
| 56: | S:0.875 |
| 57: | G:0.873 |
| 58: | I:0.595 V:0.369 |
| 59: | P:0.875 S:0.082 |
| 60: | D:0.392 E:0.326 L:0.109 |
| 61: | R:0.966 |
| 62: | F:0.967 |

TABLE 5-continued

Variable domains of the light chain of the lambda type
of humans
Determined consensus sequence (SEQ ID NO: 5)
1 QSELTQPPS-VSVSPGQTVTISCSGDSLGIG - - - YVSWYQQKPGQAPKLVIYD
51 DNKRPSGIPDRFSGSKSGHTASLTISGLQAEDEADYYCQSWDSSS - - - VVFGG
101 GTKLTVLGQP
(SEQ ID NO:5 shows the consensus sequence without inserts)

| Position | Type and frequency |
|---|---|
| 63: | S:0.999 |
| 64: | G:0.913 |
| 65: | S:0.974 |
| 66: | K:0.437 S:0.193 N:0.190 |
| 67: | S:0.959 |
| 68: | G:0.859 |
| 69: | N:0.520 T:0.242 |
| 70: | T:0.565 S:0.275 |
| 71: | A:0.913 |
| 72: | S:0.491 T:0.436 |
| 73: | L:0.999 |
| 74: | T:0.812 A:0.116 |
| 75: | I:0.945 |
| 76: | S:0.718 T:0.208 |
| 77: | G:0.828 R:0.120 |
| 78: | L:0.534 V:0.194 A:0.154 T:0.117 |
| 79: | Q:0.656 E:0.165 |
| 80: | A:0.460 S:0.175 T:0.171 V:0.127 |
| 81: | E:0.573 G:0.174 |
| 82: | D:0.971 |
| 83: | E:0.993 |
| 84: | A:0.974 |
| 85: | D:0.908 |
| 86: | Y:0.999 |
| 87: | Y:0.817 F:0.183 |
| 88: | C:0.999 |
| 89: | Q:0.473 S:0.203 |
| 90: | S:0.524 T:0.208 A:0.190 |
| 91: | W:0.438 Y:0.336 |
| 92: | D:0.590 |
| 92: | S:0.388 N:0.160 0:0.148 |
| 94: | S:0.537 G:0.156 |
| 95: | S:0.245 G:0.167 L:0.158 |
| 95a: | -:0.343 S:0.156 N:0.103 |
| 95b: | -:0.590 |
| 95c: | -:0.941 |
| 95d: | -:0.992 |
| 95e: | -:1.000 |
| 95f: | -:1.000 |
| 96: | V:0.344 P:0.101 |
| 97: | V:0.715 I:0.152 L:0.111 |
| 98: | F:0.999 |
| 99: | G:0.999 |
| 100: | G:0.808 |
| 101: | G:1.000 |
| 102: | T:0.999 |
| 103: | K:0.779 |
| 104: | L:0.669 V:0.330 |
| 105: | T:0.915 |
| 106: | V:0.999 |
| 106a: | L:0.968 |
| 107: | G:0.728 R:0.205 |
| 108: | Q:0.993 |
| 109: | P:0.993 |

TABLE 6

Variable domains of the light chain of the lambda type
of the mouse:
Determined consensus sequence: (SEQ ID NO: 6)
1 QAVVTQESA-LTTSPGETVTLTCRSSTGAVTTSN - - - YANWVQEKPDHLFTGLIGG
51 TNNRAPGVPARFSGSLIGDKAALTITGAQTEDEAIYFCALWYSNH - - - WVFGG
101 GTKLTVLGQP
(SEQ ID NO:6 shows the consensus sequence without inserts)

| Position | Type and frequency |
|---|---|
| 1: | Q:0.966 |
| 2: | A:0.999 |
| 3: | V:1.000 |
| 4: | V:0.999 |
| 5: | T:1.000 |
| 6: | Q:1.000 |
| 7: | E:0.894 Q:0.105 |
| 8: | S:1.000 |
| 9: | A:0.999 |
| 10: | -:1.000 |
| 11: | L:0.999 |
| 12: | T:0.999 |
| 13: | T:0.999 |
| 14: | S:1.000 |
| 15: | P:0.999 |
| 16: | G:0.994 |
| 17: | E:0.655 G:0.344 |
| 18: | T:0.999 |
| 19: | V:0.999 |
| 20: | T:0.646 I:0.353 |
| 21: | L:1.000 |
| 22: | T:0.990 |
| 23: | C:1.000 |
| 24: | R:0.999 |
| 25: | S:0.999 |
| 26: | S:0.800 T:0.175 |
| 27: | T:0.888 S:0.112 |
| 28: | G:0.999 |
| 29: | A:0.999 |
| 30: | V:0.991 |
| 31: | T:1.000 |
| 31a: | T:0.989 |
| 31b: | S:0.925 |
| 31c: | N:0.999 |
| 31d: | -:1.000 |
| 31e: | -:1.000 |
| 31f: | -:1.000 |
| 32: | Y:0.999 |
| 33: | A:0.999 |
| 34: | N:0.990 |
| 35: | W:1.000 |
| 36: | V:0.919 |
| 37: | Q:1.000 |
| 38: | E:0.865 Q:0.135 |
| 39: | K:0.999 |
| 40: | P:0.990 |
| 41: | D:0.999 |
| 42: | H:0.999 |
| 43: | L:0.999 |
| 44: | F:0.999 |
| 45: | T:0.990 |
| 46: | G:0.999 |
| 47: | L:0.990 |
| 48: | I:0.982 |
| 49: | G:0.999 |
| 50: | G:0.984 |
| 51: | T:0.992 |
| 52: | N:0.609 S:0.343 |
| 53: | N:0.844 |
| 54: | R:0.999 |
| 55: | A:0.859 T:0.105 |
| 56: | P:0.999 |
| 57: | G:1.000 |
| 58: | V:0.999 |
| 59: | P:1.000 |
| 60: | A:0.632 V:0.367 |
| 61: | R:1.000 |
| 62: | F:1.000 |

TABLE 6-continued

Variable domains of the light chain of the lambda type
of the mouse:
Determined consensus sequence: (SEQ ID NO: 6)
1 QAVVTQESA-LTTSPGETVTLTCRSSTGAVTTSN - - - YANWVQEKPDHLFTGLIGG
51 TNNRAPGVPARFSGSLIGDKAALTITGAQTEDEAIYFCALWYSNH - - - WVFGG
101 GTKLTVLGQP
(SEQ ID NO:6 shows the consensus sequence without
inserts)

| Position | Type and frequency |
|---|---|
| 63: | S:1.000 |
| 64: | G:1.000 |
| 65: | S:1.000 |
| 66: | L:0.999 |
| 67: | I:0.999 |
| 68: | G:1.000 |
| 69: | D:0.888 N:0.110 |
| 70: | K:0.999 |
| 71: | A:0.999 |
| 72: | A:0.999 |
| 73: | L:1.000 |
| 74: | T:0.999 |
| 75: | I:-1.000 |
| 76: | T:0.999 |
| 77: | G:0.999 |
| 78: | A:0.928 |
| 79: | Q:1.000 |
| 80: | T:0.999 |
| 81: | E:1.000 |
| 82: | D:1.000 |
| 83: | E:0.657 D:0.343 |
| 84: | A:1.000 |
| 85: | J:0.615 M:0.385 |
| 86: | Y:1.000 |
| 87: | F:0.999 |
| 88: | C:1.000 |
| 89: | A:0.992 |
| 90: | L:0.999 |
| 91: | W:0.999 |
| 92: | Y:0.897 |
| 93: | S:0.895 |
| 94: | N:0.763 T:0.236 |
| 95: | H:0.929 |
| 95a: | -:0.976 |
| 95b: | -:0.999 |
| 95c: | -:0.999 |
| 95d: | -:0.999 |
| 95e: | -:1.000 |
| 95f: | -:1.000 |
| 96: | W:0.510 F:0.327 Y:0.107 |
| 97: | V:0.767 I:0.176 |
| 98: | F:1.000 |
| 99: | G:0.936 |
| 100: | G:0.841 S:0.159 |
| 101: | G:1.000 |
| 102: | T:0.996 |
| 103: | K:1.000 |
| 104: | L:0.549 V:0.451 |
| 105: | T:1.000 |
| 106: | V:1.000 |
| 106a: | L:1.000 |
| 107: | G:1.000 |
| 108: | Q:0.874 X:0.126 |
| 109: | P:1.000 |

What is claimed is:

1. A process for improving the stability of an antibody variable domain by modifying an initial antibody variable domain, the process comprising the following steps:
   (A) providing an initial gene encoding an amino acid sequence of an initial variable domain to be modified;
   (B) comparing the amino acid sequence encoded by the initial gene with one of consensus tables 1–6, wherein
      (1) the amino acid sequence of a variable domain of a heavy chain of a human antibody is compared with consensus table 1,
      (2) the amino acid sequence of a variable domain of a heavy chain of a mouse antibody is compared with consensus table 2,
      (3) the amino acid sequence of a variable domain of a kappa light chain of a human antibody is compared with consensus table 3,
      (4) the amino acid sequence of a variable domain of a kappa light chain of a mouse antibody is compared with consensus table 4,
      (5) the amino acid sequence of a variable domain of a lambda light chain of a human antibody is compared with consensus table 5,
      (6) the amino acid sequence of a variable domain of a lambda light chain of a mouse antibody is compared with consensus table 6,
   (C) thereafter producing a modified gene which encodes for a modified antibody variable domain by modifying in the initial gene
      (1) at least one codon of each pair of codons which encode for cysteine bridges, so that all disulfide bridges present in the initial antibody variable domain are absent from the modified antibody variable domain, and
      (2) at least one additional codon which codes for an amino acid other than a disulfide bridge-forming cysteine is substituted by another codon using a consensus table selected in part (b) as a guide, wherein
         (I) the codon coding for the initial amino acid is modified by substituting a codon coding for a substitute amino acid which is listed in the consensus table at a position corresponding to the selected position, when the initial amino acid is unlisted in the selected consensus table at the position corresponding to the selected position, or
         (II) the codon coding for the initial amino acid is modified by substituting a codon coding for a substitute amino acid having higher frequency in the consensus table at a position corresponding to the selected position, when the initial amino acid is listed a given frequency in the consensus table at the position corresponding to the selected table, the higher frequency being compared to the given frequency;
   (D) transfecting a eukaryotic cell with the modified gene encoding the modified antibody variable domain; and
   (E) expressing in the transfected eukaryotic cell the modified antibody variable domain, wherein the modified antibody variable domain expressed by the eukaryotic cell has improved stability when compared to the stability of the initial antibody variable domain.

2. The process of claim 1, wherein the transfected eukaryotic cell expresses an antibody comprising the modified antibody variable domain.

3. The process of claim 1, wherein the transfected eukaryotic cell expresses an Fab, Fab', F(ab')$_2$ or Fv antibody fragment, a single chain antibody or a single chain Fv antibody comprising the modified antibody variable domain.

4. The process of claim 1, wherein the initial antibody variable domain is a human variable domain.

5. The process of claim 4, wherein the initial gene encodes the variable domain of a heavy chain.

6. The process of claim 4, wherein the initial gene encodes the variable domain of a kappa light chain.

7. The process of claim 4, wherein the initial gene encodes the variable domain of a lambda light chain.

8. The process of claim 1, further comprising after step (e), isolating the modified antibody variable domain from the eukaryotic cell.

9. The process of claim 8, further comprising purifying the isolated modified antibody variable domain.

10. The process of claim 1, further comprising between step (a) and step (b), sequencing the initial gene.

11. The process of claim 1, wherein in step (c), the codons are modified by mutagenesis.

12. The process of claim 1, wherein the eukaryotic cell is selected from the group consisting of a CHO cell, a lymphocyte cell, a yeast cell and an insect cell.

13. The process of claim 1, wherein the initial antibody variable domain is a mouse variable domain.

14. The process of claim 13, wherein the initial gene encodes the variable domain of a heavy chain.

15. The process of claim 13, wherein the initial gene encodes the variable domain of a kappa light chain.

16. The process of claim 13, wherein the initial gene encodes the variable domain of a lambda light chain.

17. The process of claim 1, wherein in step (c) the at least one additional codon to be modified codes for an initial amino acid at a selected position other than in an antigen binding loop.

* * * * *